(12) United States Patent
Malackowski et al.

(10) Patent No.: US 7,725,162 B2
(45) Date of Patent: May 25, 2010

(54) SURGERY SYSTEM

(75) Inventors: Donald W. Malackowski, Schoolcraft, MI (US); Jose Luis Moctezuma de la Barrere, Freiburg (DE); David E. Hershberger, Kalamazoo, MI (US); Markus Bohringer, Ehrenkirchen (DE); Peter Forst, Emmendingen (DE); Ulrich Buehner, Freiburg (DE); Martin Stangenberg, Gundelfingen (DE); Jerry A. Culp, Kalzamazoo, MI (US); Klaus Welte, Seelbach (DE)

(73) Assignee: Howmedica Leibinger Inc., Kalamazoo, MI (US)

( * ) Notice: Subject to any disclaimer, the term of this patent is extended or adjusted under 35 U.S.C. 154(b) by 1898 days.

(21) Appl. No.: 10/677,874

(22) Filed: Oct. 2, 2003

(65) Prior Publication Data

US 2004/0073279 A1 Apr. 15, 2004

Related U.S. Application Data

(62) Division of application No. 09/764,609, filed on Jan. 17, 2001, now abandoned.

(60) Provisional application No. 60/178,377, filed on Jan. 27, 2000.

(51) Int. Cl.
*A61B 19/00* (2006.01)
*A61B 17/00* (2006.01)

(52) U.S. Cl. .............................. 600/424; 600/427; 606/1

(58) Field of Classification Search ................ 600/424, 600/427, 426; 606/1, 130

See application file for complete search history.

(56) References Cited

U.S. PATENT DOCUMENTS

| | | | |
|---|---|---|---|
| 4,323,459 A | 4/1982 | Quinlan | 210/700 |
| 4,396,945 A | 8/1983 | DiMatteo et al. | 358/107 |
| 4,722,056 A | 1/1988 | Roberts et al. | 364/413 |
| 4,869,247 A | 9/1989 | Howard, III et al. | 128/303.1 |
| 4,923,459 A | 5/1990 | Nambu | 606/130 |
| 4,945,914 A | 8/1990 | Allen | 128/653 R |
| 4,951,653 A | 8/1990 | Fry et al. | 128/24 A |
| 4,991,579 A | 2/1991 | Allen | 128/653 R |
| 5,016,639 A | 5/1991 | Allen | 128/653 R |
| 5,094,241 A | 3/1992 | Allen | 128/653.1 |

(Continued)

FOREIGN PATENT DOCUMENTS

CA 2 364 122 9/2000

(Continued)

OTHER PUBLICATIONS

Birkfellner et al., "Evaluation and Detection of Systematic Distortions in DC-pulsed Electromagnetic Position Sensing Devices," *Elsevier Science B.V.*, 1998, pp. 927-928.

(Continued)

*Primary Examiner*—John P Leubecker
(74) *Attorney, Agent, or Firm*—McCracken & Frank LLP

(57) ABSTRACT

A surgery system comprising at least one smart instrument, a computer system, and a sensor system adapted to wirelessly sense the position of the at least one smart instrument and to transmit position information to the computer system, wherein the sensor system includes a sensor array and the sensor array includes at least three linear CCD cameras and at least one infrared transceiver.

5 Claims, 28 Drawing Sheets

U.S. PATENT DOCUMENTS

| | | | | |
|---|---|---|---|---|
| 5,097,839 | A | 3/1992 | Allen | 128/653.1 |
| 5,119,817 | A | 6/1992 | Allen | 128/653.1 |
| 5,142,930 | A | 9/1992 | Allen et al. | 74/469 |
| 5,178,164 | A | 1/1993 | Allen | 128/898 |
| 5,186,174 | A | 2/1993 | Schlondorff et al. | 128/653.1 |
| 5,198,877 | A | 3/1993 | Schulz | 356/375 |
| 5,211,164 | A | 5/1993 | Allen | 128/653.1 |
| 5,222,499 | A | 6/1993 | Allen et al. | 128/653.1 |
| 5,230,338 | A | 7/1993 | Allen et al. | 128/653 |
| 5,309,101 | A | 5/1994 | Kim et al. | 324/309 |
| 5,383,454 | A | 1/1995 | Bucholz | 128/653.1 |
| 5,394,875 | A | 3/1995 | Lewis et al. | 128/660.09 |
| 5,397,329 | A | 3/1995 | Allen | 606/73 |
| 5,494,034 | A | 2/1996 | Schlondorff et al. | 128/653.1 |
| 5,515,160 | A | 5/1996 | Schulz et al. | 356/241 |
| 5,551,429 | A | 9/1996 | Fitzpatrick et al. | 128/653.1 |
| 5,575,794 | A | 11/1996 | Walus et al. | 606/116 |
| 5,590,215 | A | 12/1996 | Allen | 382/128 |
| 5,595,193 | A | 1/1997 | Walus et al. | 128/898 |
| 5,617,857 | A | 4/1997 | Chader et al. | 128/653.1 |
| 5,622,170 | A | 4/1997 | Schulz | 128/653.1 |
| 5,638,819 | A | 6/1997 | Manwaring et al. | 128/653.1 |
| 5,695,501 | A | 12/1997 | Carol et al. | 606/130 |
| 5,704,897 | A | 1/1998 | Truppe | 600/117 |
| 5,711,299 | A | 1/1998 | Manwaring et al. | 128/653.1 |
| 5,730,130 | A | 3/1998 | Fitzpatrick et al. | 128/653.1 |
| 5,752,513 | A | 5/1998 | Acker et al. | 128/653.1 |
| RE35,816 | E | 6/1998 | Schulz | 356/376 |
| 5,769,789 | A | 6/1998 | Wang et al. | 600/414 |
| 5,797,924 | A | 8/1998 | Schulte et al. | 606/130 |
| 5,799,099 | A | 8/1998 | Wang et al. | 382/131 |
| 5,851,183 | A | 12/1998 | Bucholz | 600/425 |
| 5,871,445 | A | 2/1999 | Bucholz | 600/407 |
| 5,891,034 | A | 4/1999 | Bucholz | 600/426 |
| 5,891,157 | A | 4/1999 | Day et al. | 606/130 |
| 5,907,395 | A | 5/1999 | Schulz et al. | 356/139.03 |
| 5,916,164 | A | 6/1999 | Fitzpatrick et al. | 600/426 |
| 5,921,992 | A | 7/1999 | Costales et al. | 606/130 |
| 5,954,648 | A | 9/1999 | Van Der Brug | 600/411 |
| 5,970,499 | A | 10/1999 | Smith et al. | 707/104 |
| 5,987,349 | A | 11/1999 | Schulz | 600/427 |
| 5,987,960 | A * | 11/1999 | Messner et al. | 73/1.79 |
| 6,073,044 | A | 6/2000 | Fitzpatrick et al. | 600/426 |
| 6,081,336 | A | 6/2000 | Messner et al. | 356/375 |
| 6,092,722 | A | 7/2000 | Heinrichs et al. | |
| 6,112,113 | A | 8/2000 | Van Der Brug et al. | 600/427 |
| 6,226,548 | B1 * | 5/2001 | Foley et al. | 600/426 |
| 6,306,126 | B1 * | 10/2001 | Moctezuma | 606/1 |
| 6,366,622 | B1 | 4/2002 | Brown et al. | 375/322 |
| 6,405,072 | B1 * | 6/2002 | Cosman | 600/426 |
| 6,453,190 | B1 | 9/2002 | Acker et al. | 600/424 |
| 6,618,612 | B1 * | 9/2003 | Acker et al. | 600/424 |
| 6,675,040 | B1 * | 1/2004 | Cosman | 600/427 |
| 6,697,664 | B2 * | 2/2004 | Kienzle, III et al. | 600/427 |
| 7,217,276 | B2 * | 5/2007 | Henderson et al. | 606/130 |
| 2003/0073901 | A1 * | 4/2003 | Simon et al. | 600/424 |

FOREIGN PATENT DOCUMENTS

| | | |
|---|---|---|
| DE | 3904595 | 4/1990 |
| DE | 196 29 646 | 1/1998 |
| DE | 299 04 018 | 6/1999 |
| EP | 326768 | 8/1989 |
| JP | 3267054 | 11/1991 |
| JP | 6282889 | 10/1994 |
| JP | 6282890 | 10/1994 |
| WO | WO 90/05494 | 5/1990 |
| WO | WO 00/39576 | 7/2000 |

OTHER PUBLICATIONS

Birkfellner et al., "Systematic Distortions in Magnetic Position Digitizers," *Med. Phys.* 25 (11), pp. 2242-2248 (Nov. 1998).

Livingston et al., "Magnetic Tracker Calibration for Improved Augmented Reality Registration," *Presence*, vol. 6, No. 5, pp. 532-546 (Oct. 1997).

State et al., "Superior Augmented Reality Registration by Integrating Landmark Tracking and Magnetic Tracking," Proceedings of SIG-GRAPH 96 (New Orleans, LA, Aug. 4-9, 1996). In *Computer Graphics* Proceedings, Annual Conference Series, pp. 429-438.

Birkfellner et al., "Calibration of Tracking Systems in a Surgical Environment," *IEEE Tansactions on Medical Imaging*, Nov. 17, 1998, pp. 1-6.

Birkfellner et al., "Evaluation of Magnetic Position Digitizers for Computer Assisted Surgery," *Comput. Aided Surg.* 2(3/4), 225 (1997).

International Search Report dated Aug. 15, 2001, Int'l. Appl. No. PCT/US01/02166.

PCT Written Opinion, Appl. No. PCT/US01/02166, dated Jan. 2, 2002.

Applied Neurophysiology, Journal of Stereotactic and Functional Neurosurgery, Proceedings of the Meeting of the American Society for Stereotactic and Functional Neurosurgery, Montreal, Quebec, (Jun. 3-6, 1987) Jan. 1998.

Stereotactic & Functional Neurosurgery vol. 53, No. 3, (1989) pp. 197-201.

Journal of Ultrasound in Medicine vol. 9, No. 9, (Sep. 1990), pp. 525-532.

Ultrasound in Neurosurgery J.M. Rubin et al. ISBN: 0881675490, pp. 47-58.

Stereotactic & Functional Neurosurgery vol. 54-55, (1990), pp. 419, 422, 423, 471-476, 482-487, 488-492, 493-496, 497, 498, 500.

British Journal of Neurosurgery vol. 4, No. 3, (1990), pp. 193-197.

IEEE Computer Graphics & Applications vol. 3, No. 10, (May 1990), pp. 43-51.

Journal of Neurosurgery vol. 72, No. 2, (Feb. 1990), pp. 355a.

IEEE Engineering in Medicine & Biology Society—Proceedings of 11th Annual International Conference, (1989), pp. 925, 926-929.

British Journal of Neurosurgery vol. 3, No. 5, (1989), pp. 561-568, 569-574.

British Journal of Neurosurgery vol. 3, No. 3, (1989), pp. 327-331.

Acta Neurochirurgica Supplementum 46, (1989), pp. 112-114.

Journal of Neurosurgery vol. 65, No. 4, (Oct. 1986), pp. 550-554, 557-559.

Journal of Neurosurgery vol. 57, No. 2, (Aug. 1982), pp. 157-163.

Neurosurgery vol. 10, No. 5, (May 1982), pp. 580-586.

Neurosurgery vol. 10, (Mar. 1982), pp. 375-379.

Guided Brain Operations E.A. Spiegel ISBN: 3805534515, (1982), pp. 23, 25, 28.

American Journal of Neuroradiology vol. 2, No. 2 (Mar./Apr. 1981), pp. 181-184.

Neurosurgery vol. 8, No. 1 (Jan. 1981), pp. 72-82.

Surgical Neurology vol. 14, No. 6, (Dec. 1980), pp. 451-464.

Investigative Radiology vol. 15, No. 4, (Jul./Aug. 1980), pp. 308-312.

Applied Neurophysiology vol. 43, No. 3-5, (1980), pp. 170-171, 172-173, 174-175.

Neurosurgery vol. 3, No. 2, (Sep./Oct. 1978), pp. 157-161.

Supplementary European Search Report in EP 01 90 3234 dated Jun. 13, 2008.

Office Action dated Dec. 19, 2008 for European Application No. 01 90 3234.1.

* cited by examiner

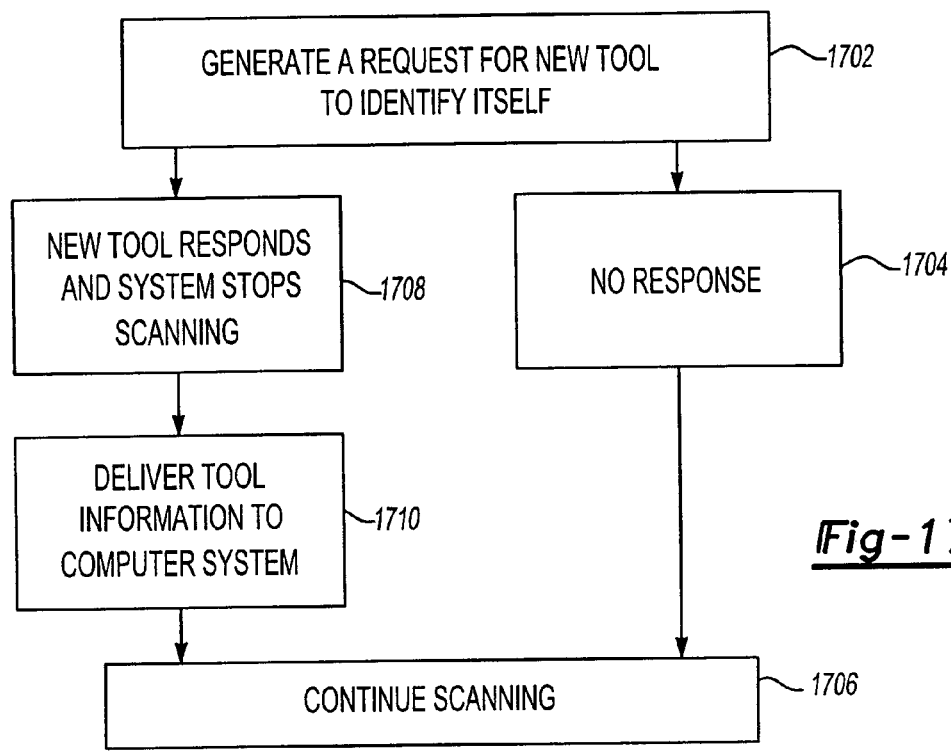
Fig-16
Fig-17
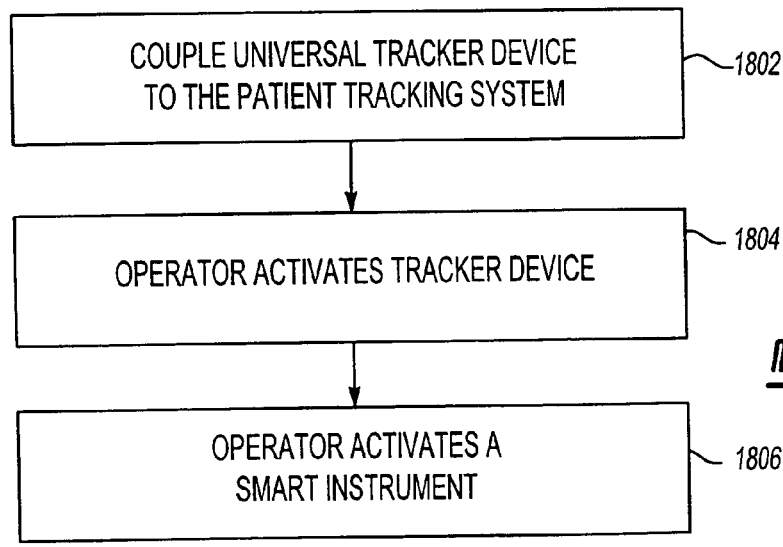
Fig-18

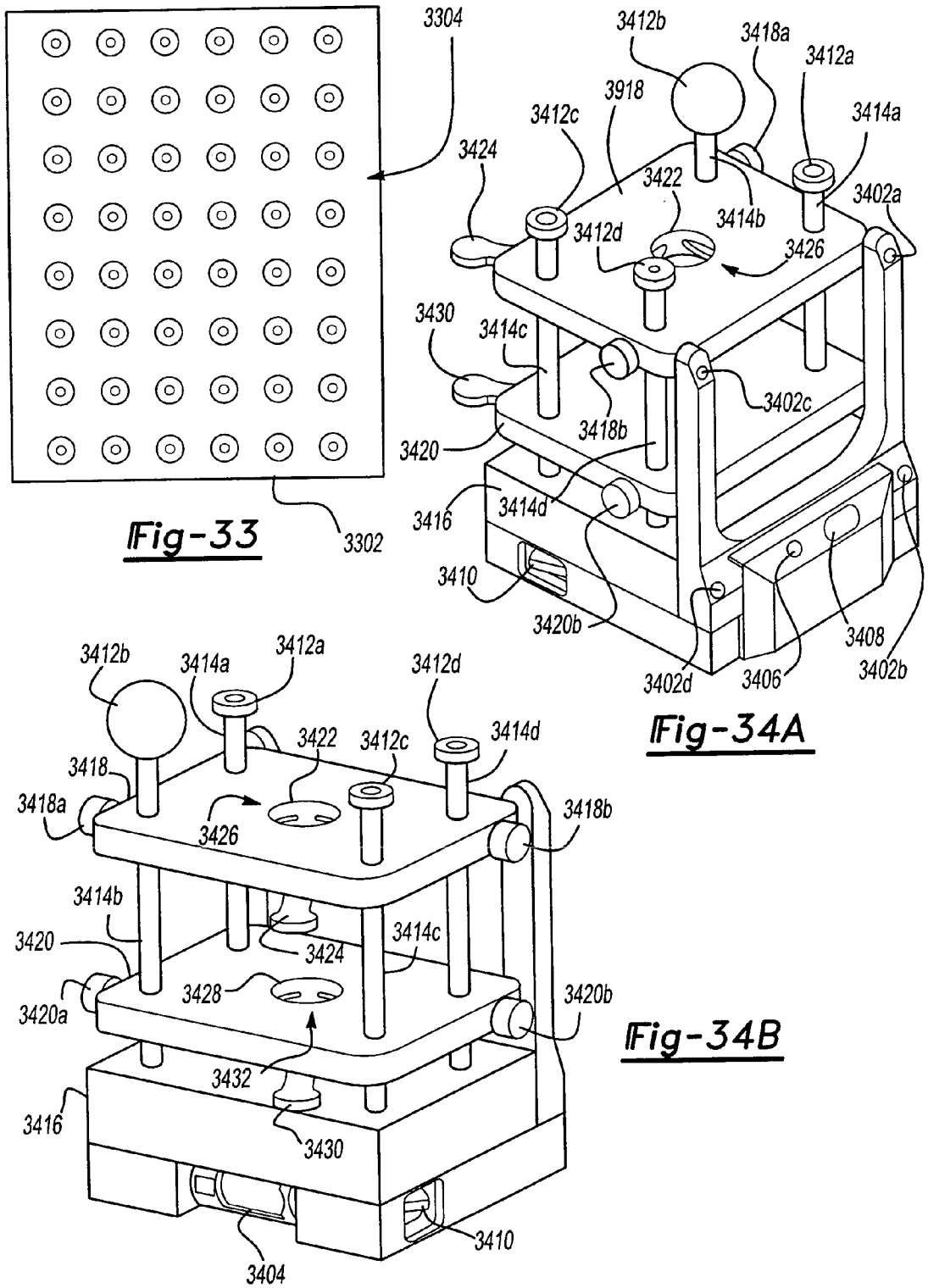

SURGERY SYSTEM

This application is a divisional of U.S. application Ser. No. 09/764,609, filed on Jan. 17, 2001, and now abandoned, which claims priority from provisional application Ser. No. 60/178,377, filed on Jan. 27, 2000.

BACKGROUND OF THE INVENTION

1. Field of the Invention

This invention relates generally to a surgery system. In particular this invention relates to a system for displaying and guiding a series of instruments to a surgical site located relative to a body of a patient.

2. Description of Related Art

Traditionally, an image-guided surgery system is used to display a position of a surgical instrument in an operating zone within the body of a patient. A number of frame and frameless stereotactic systems have been developed to assist surgeons during various procedures that require an instrument to travel to a target within a body. Typically, a surgeon analyzes images of the body using CT scans, MRI scans, or PET scans to determine a location of a target and to determine a desirable trajectory along which the instrument should travel during a surgical procedure. The image-guided surgery system includes a position measuring system for measuring the position of the surgical instrument. A typical image guided system usually includes a series of surgical instruments, a computer system, a camera or other localization device, a monitor, a cabinet or stand to hold the monitor and computer, and various connecting equipment and accessories. The computer system is used for calculating the positions of the instruments in a corresponding previously captured or real time image of a surgical site. The position of the instrument is displayed on the image of the surgical site on the monitor. The image on the monitor shows the surgeon exactly where in the operating zone the surgical instrument is located, without the surgeon having a direct view of the instrument. Image guided systems improve the accuracy and efficiency of many surgical procedures such as complex, sight impaired neurological procedures. Known frameless stereotactic systems utilize optical, RF, magnetic, audio, or other signal systems to communicate between the surgical instruments and the computer system. Typically, the surgical instruments are either tethered to the computer system or are wireless. Wireless instruments carry a system-compatible emitter or sensor for communication through LEDs or RF systems to the computer system. Tethered instruments can add complexity to the system by limiting the range of motion of the instrument and adding additional wires and cables to route and negotiate during the surgery. Range of motion of the instrument is very important during the surgery itself. Limitations must be overcome by the surgeon and can lead to inaccuracies in the surgery.

Traditional image guided systems require a lengthy set up process whereby the user registers reference points of the pre-established image, initializes and calibrates the instruments, and registers a plan of trajectory for the instruments. The initialization and calibration of the instruments is critical to the proper operation of the system and can involve numerous steps and manipulations by the users. Calibration of traditional systems involve field calibration units that must be brought to the instruments to be calibrated. Additional software is also often required to be installed in order to calibrate a new instrument. Re-calibrations are often required during surgery if a new instrument is necessary or if an instrument is dropped or damaged during use. Keeping the calibration software up to date, and all of the instruments in proper working order during the surgery is critical. Traditional systems also maintain one set of software code for calibrating a specific type of instrument. However, if there is a flaw in the instrument due to a manufacturing flaw or a flaw caused during use, the software may not be able to recognize the instrument, thereby making rendering the instrument useless.

Many traditional systems require the manual entry of initialization and calibration information into the computer system. This process is lengthy and if not performed properly can result in inaccuracies in the imaging system.

During surgery, many traditional image guided systems necessitate multiple operators, one to manipulate the instruments within the sterile field and another to make changes to the equipment and operate the computer system which is often outside of the sterile field or beyond reach of the surgeon operating the instruments. The use of multiple operators may lead to inaccuracies in the system and inefficiencies in the operation.

The sterilization of surgical equipment is an additional requirement that has traditionally affected the efficacy of the instruments and other components. Known stereotactic systems typically utilize system-specific surgical instruments that incorporate some type of location sensor or emitter. These surgical instruments must be sterilized carefully to ensure that the sensitive detection equipment is not damaged. Due to the high cost of such equipment, surgeons must sterilize and reuse the surgical instrument rather than dispose of the sensor or emitter components after each use. The battery life of the instruments may also be affected by the sterilization process and limited battery life can impact the surgery if an instrument loses power during use.

Thus, what is desired is an improved image guided system that would improve and address these concerns. An improved system would provide improved control, use, life, and precision of the instruments and would allow for easier set up and use of the system overall. The improved system would enhance component compatibility and interchangeability, and improve the economic efficiency of the image guided surgery system.

BRIEF SUMMARY OF THE INVENTION

It is an object of the invention to provide an image-guided surgery system which enables easy, fast and accurate initialization, calibration, and control of a series of image guided surgery instruments. This object is achieved by providing wireless instruments with several improvements. The instruments of this invention are wireless and have a bi-directional high speed communication system that allows communication between the instruments and a computer system in real time. The communication system consists of a high-speed, specific frequency or spread frequency, infrared or RF based signaling system located in the instruments and a second signaling system connected to the computer. The instruments contain non-volatile memory circuitry allowing the instruments themselves to store information about the instrument and communicate that information back to the computer system through a communication path. The instruments memory consists of an updateable EE Ram structure that can be completely updated or changed at any time. This feature allows the instruments of the invention to be updated with an improved software package as the system design changes over time. This improves an instrument's life and reduces a lifetime cost of the image-guided surgery system.

The image-guided system's communication path allows the downloading of calibration data from the instruments to the computer system and uploading of calibration information to the instruments from the computer system. Control data can also be downloaded to the instrument instructing the instrument to perform a function, such as irrigation. The patient tracker of the invention includes a zero tolerance adapter interface for connection of the tracker to an instrument adapter or reference frame. This allows for patient setup and registration to be completed with non-sterile instruments.

The improved communication path allows the improved instruments to be calibrated much easier and faster than conventional instruments. By storing the calibration information in the instruments themselves the image-guided system of the invention is capable of re-calibrating damaged or imperfect instruments without going through a complex field calibration process. The computer system of the invention will recognize an error present in the instruments and re-calibrate the instrument based on the data received from the field calibration tool, eliminating a need to remove the instrument from service to perform a lengthy re-calibration procedure. The ability to store an instruments calibration and emitter positions within each individual instrument also eases a manufacturing process that traditionally required the instruments to be manufactured to a tight tolerance.

The instruments' communication and storage capabilities also allow the computer system to automatically recognize the instruments as they are placed into a field created by the localization system. The camera detection system consists of one or a plurality of camera sensors placed in a movable sensor array assembly attached to a computer system. The camera sensors contain their own calibration data allowing the camera to be apart from the computer system. The sensor array establishes a field of detection whereby the infrared signals from the instruments are received by the sensor array. The communication path of the invention allows for near instantaneous perception of a new instrument entering the field of detection. This allows the instrument to be immediately recognized and displayed by the computer system on an image of a surgical site displayed on a monitor. This feature allows a user to immediately use a new instrument without installing any new software or calibration files onto the computer system. The instrument communication system also communicates an instrument status to the computer system displaying instrument status information such as a battery and LED status to a user.

Another object of the invention is an improved control interface between the user operating the instruments and the computer system. The invention accomplishes this object by providing operating controls integrated into the instruments. Using the wireless communication system and control buttons located on the instruments, the user can operate the computer system software from a surgical field without the need for an additional assistant to operate the computer system outside the surgical field. The control buttons can also be used to control auxiliary equipment connected to the system. The function of the instrument buttons can be specifically configured by the user to customize the instruments for each user. The invention image-guided surgery system also includes a separate remote control unit that allows further control of the computer system from within the surgical field. The remote control operates using the same communication system as the instruments.

An additional object of the invention is to provide an improved image-guided surgery computer cart assembly for housing the computer system, the monitor, the camera detection system, and organizing a plurality of power supply cables and a plurality of communication cables. The computer cart of the invention includes an interface for connecting communication cables from the monitor and the camera detection system to the computer. In addition the cart system includes an interface for connecting peripheral equipment such as a network connection, a telephone line, a plurality of microscopes, and other operating room equipment. The cart contains a monitor interface combining the low voltage power supply, video, audio, and control cables from the system into a single system power cable exiting from the cart. The cart also contains a plurality of storage locations for peripheral equipment.

BRIEF DESCRIPTION OF THE SEVERAL VIEWS OF THE DRAWINGS

FIG. 16 is a flow diagram of a smart instrument activation process, according to an embodiment of the present invention;

FIG. 17 is a second flow diagram of a smart instrument activation process, according to an embodiment of the present invention;

FIG. 18 is a flow diagram of a patient tracking system using a universal tracker device activation process, according to an embodiment of the present invention;

FIG. 33 is a diagrammatic illustration of a flexible sheet or mesh having a plurality of markers, according to an embodiment of the present invention;

FIG. 34A is a perspective view of a calibration and validation tool, according to an embodiment of the present invention;

FIG. 34B is a second perspective view of the calibration and validation tool of FIG. 34A;

DETAILED DESCRIPTION OF THE INVENTION

Figure 1:
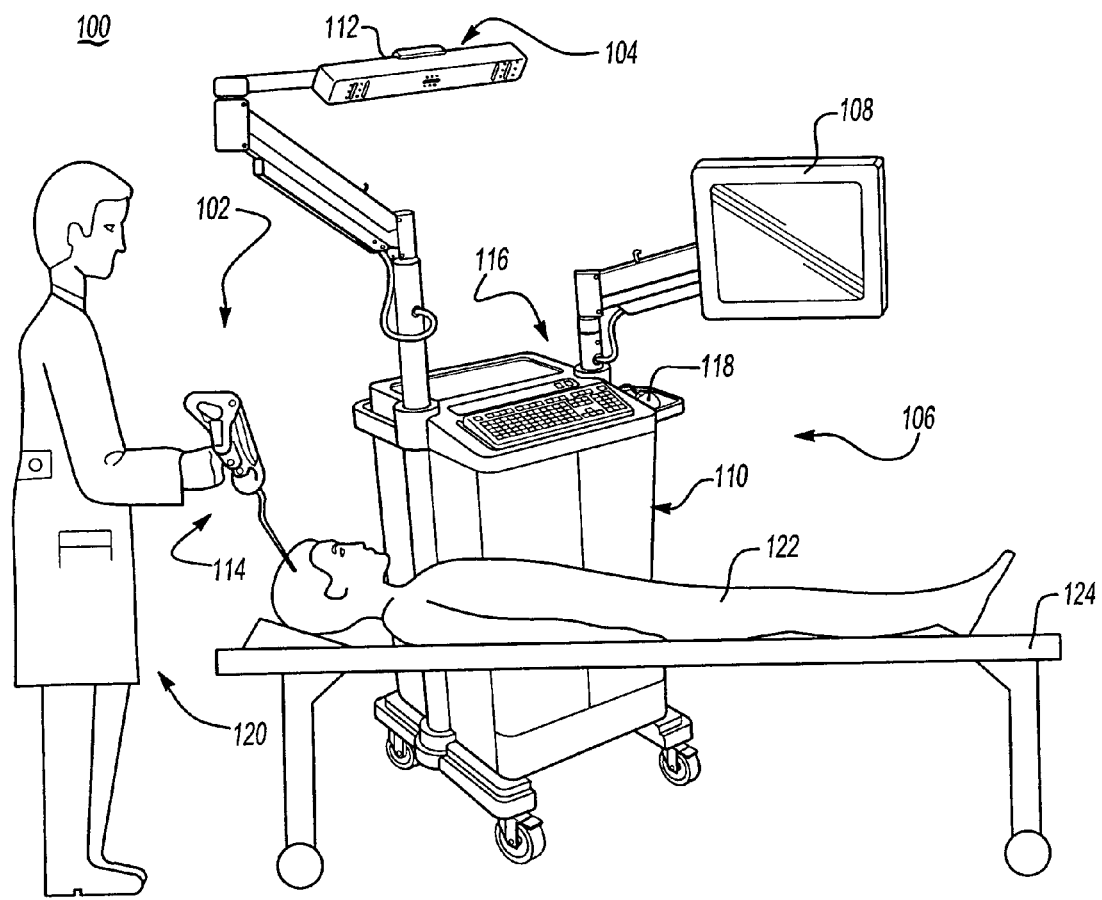
FIG. 1 is a perspective view of a surgery system according to an embodiment of the present invention.

With reference to drawings and in operation, the present invention provides a surgery system 100 having at least one smart instrument 102. The surgery system 100 includes a sensor system 104 and a computer system 106. The computer system 106 includes a monitor 108. The computer system 106 is preferably housed in a computer cart assembly 110.

The sensor system 104 is coupled to the computer system 106 and is adapted to wirelessly transmit data back and forth between the at least one smart instrument 102 and the computer system 104 and to sense the position of the at least one smart instrument 102 (see below). Preferably, the sensor system 104 comprises a sensor array 112.

The smart instrument 102 is operated by an operator 120 to display a location of the smart instrument 102 relative to a patient 122 on a diagram, e.g., an image (such as an MRI or x-ray), picture, outline, line drawing, displayed on the monitor 108 during a surgical procedure.

Figure 12:
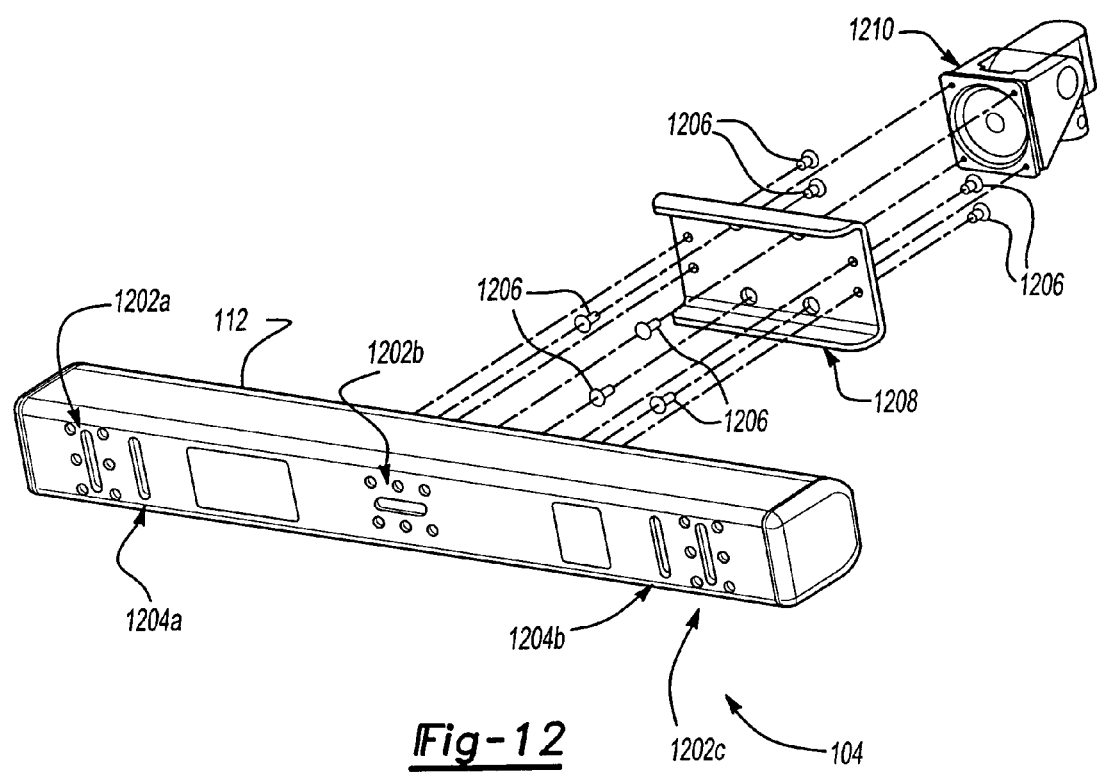
FIG. 12 is an assembly view of a sensor array for use with the surgery system of FIG. 1, according to an embodiment of the present invention.

With reference to FIG. 12, the sensor array 112 includes first, second, and third position sensors 1202a,1202b,12102c for sensing the X, Y, and Z position of a smart instrument 102. In the preferred embodiment, the first, second, and third position sensors 1202a,1202b,1202c are linear CCD cameras which are adapted to detect infrared (IR) signals generated by the smart instruments 102 (see below).

At least one infrared transceiver 1204a,1204b is used to communicate data to and from the smart instruments 102. In the preferred embodiment, the sensor array 112 includes first and second spaced apart transceivers 1202a,1202b.

The smart instruments 102 and the transceivers 1204a, 1204b communicate via infrared signals. Preferably, the infrared signals have a baud rate at a preferred frequency of 62.5 KHz and data is transmitted using an amplitude-shift keying (ASK) modulating method at a frequency of 1.5 MHz. Although the present invention will now be described as communicating wirelessly using infrared signals, other types of wireless technologies may also be used. In another embodiment, radio frequency signals are used. In still another embodiment, communication between the smart instruments 102 and the system 100 is accomplished using the IEEE 802.11 standard, commonly referred to as "Blue Tooth".

Returning to FIG. 1, the computer system 104 may be controlled remotely by a series of control buttons 114 located on the smart instrument 102. The computer system 106 also contains a keyboard 116 and a mouse 118 for operating the computer system 104.

As shown, the surgery system 100 is designed to be used by an operator 120 during a procedure on a patient 122. Preferably, the patient 122 is located on a surgical bed or table 124.

Figure 4:
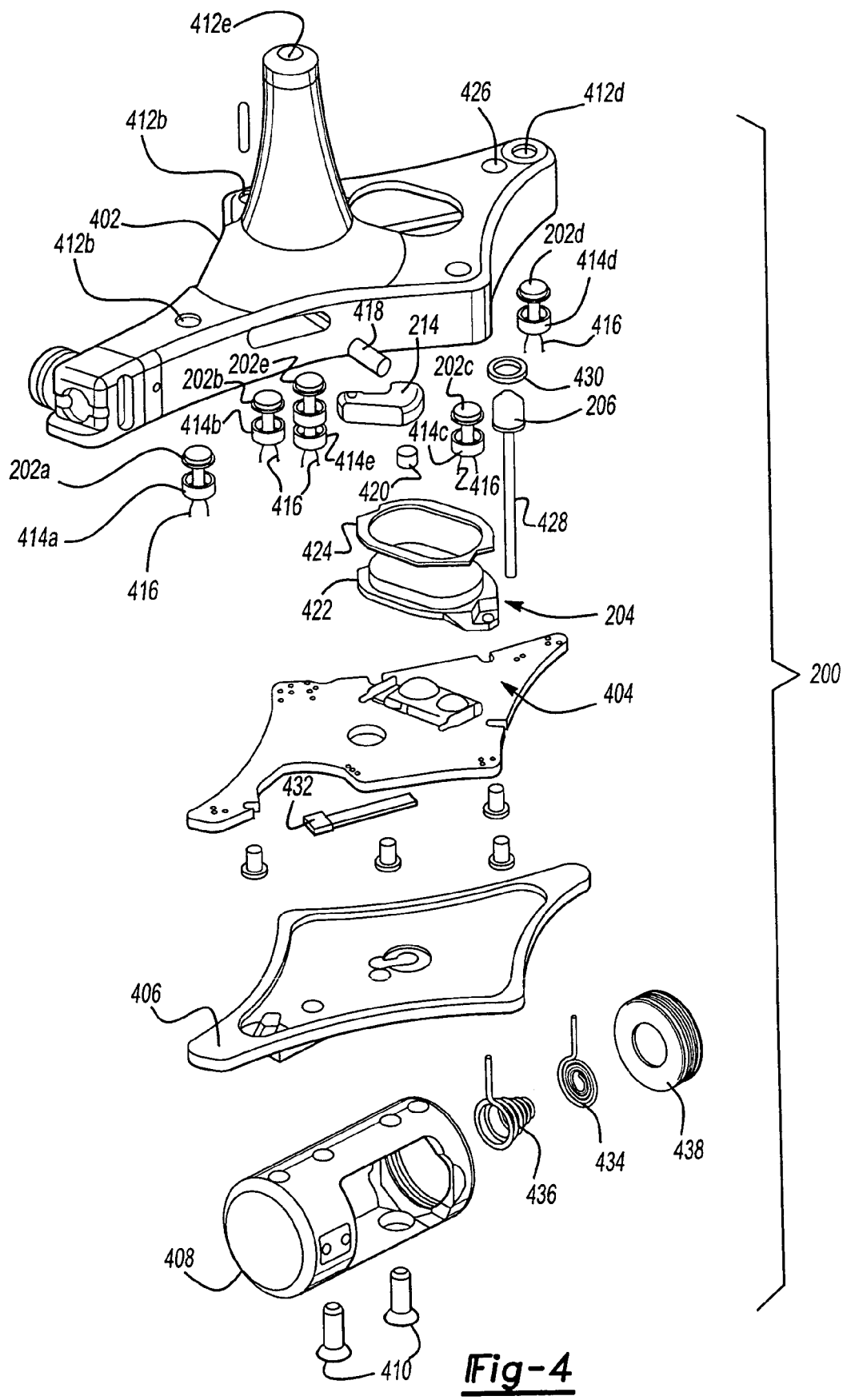
FIG. 4 is an assembly view of the universal tracker device of FIG. 2.
Figure 5:
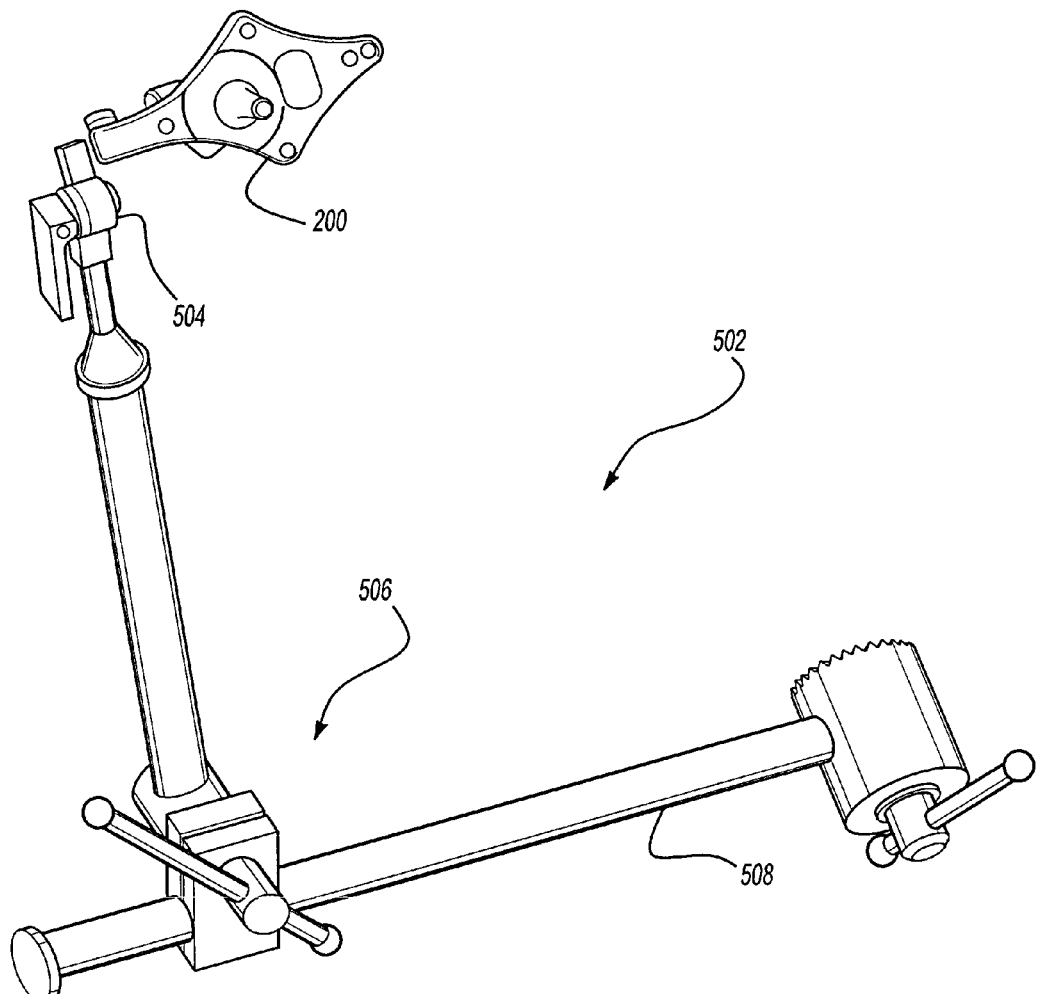
FIG. 5 is a perspective view of the universal tracker of FIG. 2 and a portion of a patient tracking system.
Figure 6:
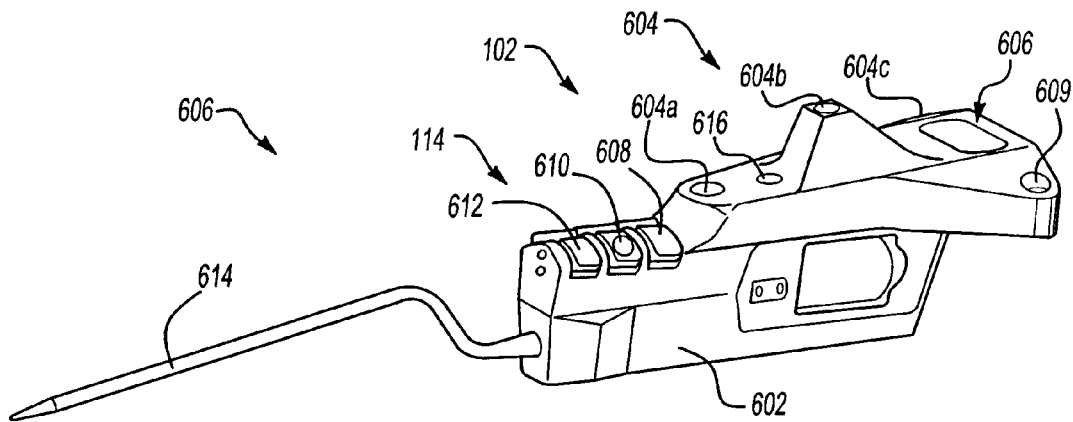
FIG. 6 is a perspective view of a smart instrument in the form of a pointer device, according to an embodiment of the present invention.
Figure 7:
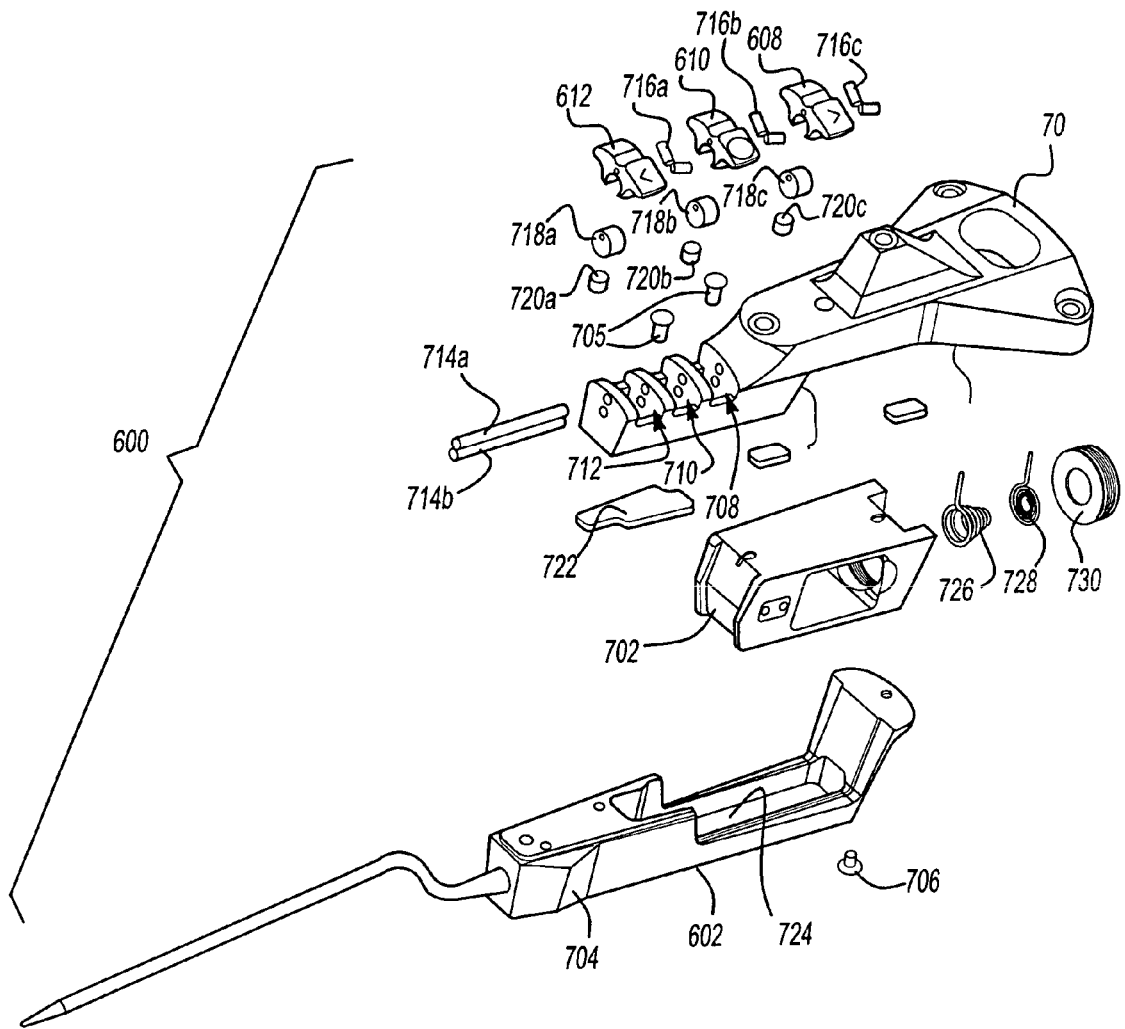
FIG. 7 is a partial assembly view of the smart instrument of FIG. 6.
Figure 8:
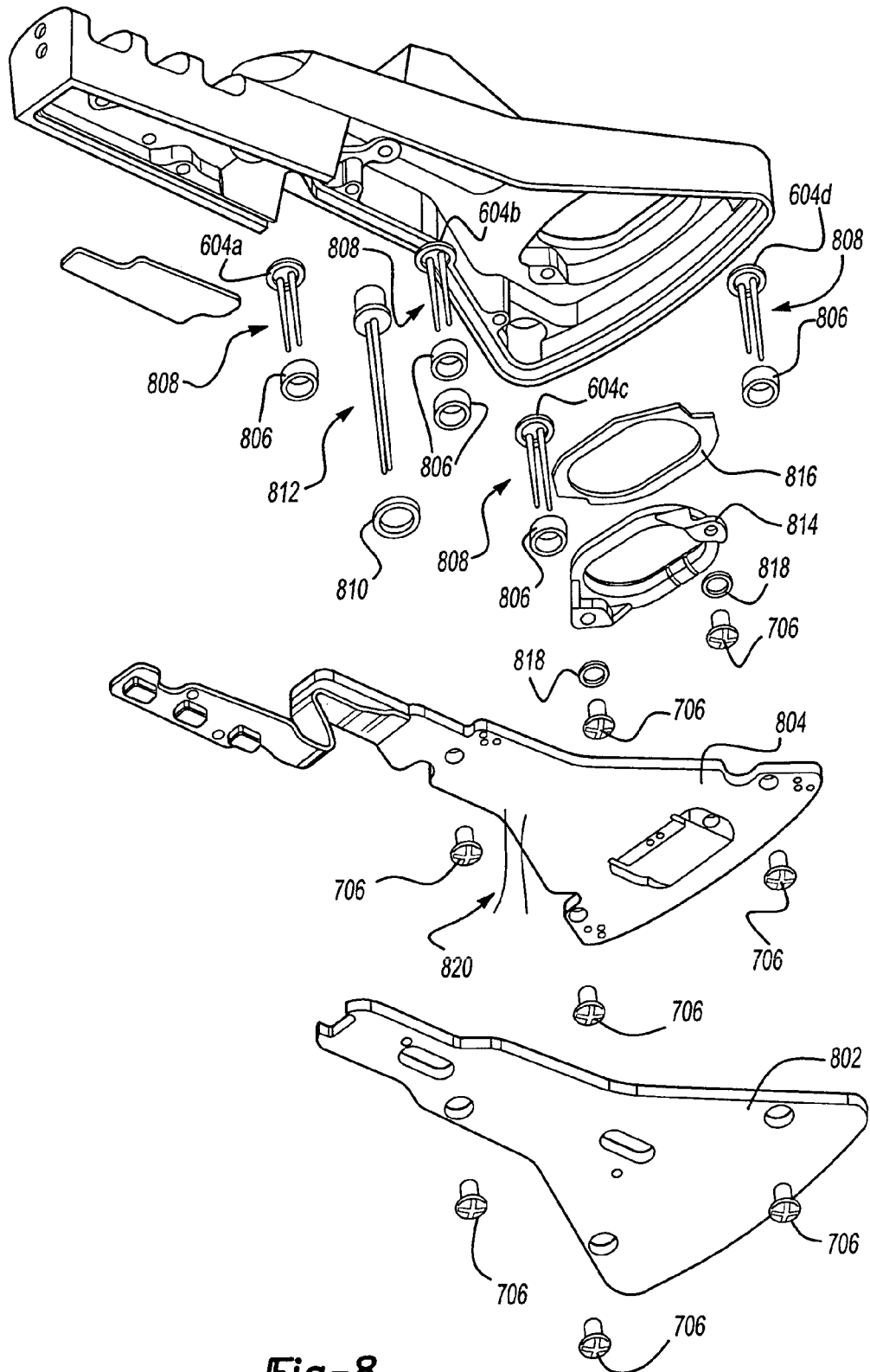
FIG. 8 is another partial assembly view of the pointer device of FIG. 6.

With reference to FIGS. 2-7, in the preferred embodiment the system 100 includes two types of smart instruments 102, a universal tracker 200, as shown in FIGS. 2-5 and a specially adapted or specific purpose instrument, such as a pointer instrument 500, as shown in FIGS. 6-8.

With reference to FIGS. 2-5, the universal tracker device 200 is shown in detail. The universal tracker device 200 may serve several functions.

First, the universal tracker device 200 allows common surgical instruments to be used with the image guided surgery system 100. Additionally, as shown In FIG. 5, the universal tracker device 200, as part of a patient tracking system 502 (shown in part), is used to initialize and calibrate a dynamic reference frame centered on the patient 122. The dynamic reference frame remains fixed relative to the patient 122 and is adjusted relative to the operating room or computer system 104 as the body moves or is moved relative thereto.

Additionally, the universal tracker device 200 is used to validate other smart instruments 102 (see below).

With specific reference to FIG. 5, the universal tracker device 200 serves as part of the patient tracking system 502. The patient tracking system 502 includes the tracker device 200, an adapter 504 and a clamp device 506 for attaching the tracker device 200 to a patient reference frame 508. A preferred clamp device is known to those skilled in the art as a Mayfield clamp. The patient reference frame 508 couples the patient tracking system 502 to the patient 122 and is adapted to move with the patient 122 as the patient moves or is moved. An example of a patient reference frame 508 is a halo.

The tracker device 200 is also used as a reference for communication between the surgical instruments and the computer system 104. The tracker device 200 is constructed of a metal material and has a geometry designed to maximize the accuracy of the localizing system.

Figure 2:
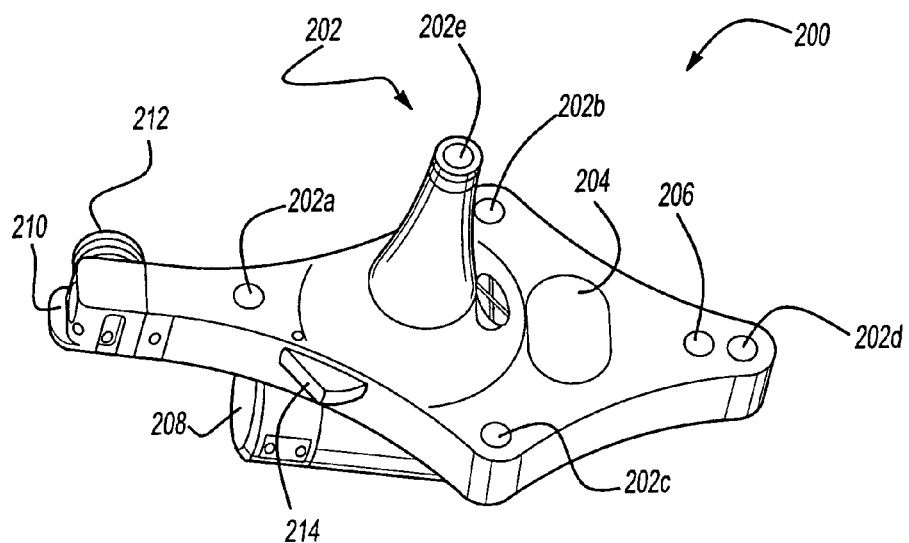
FIG. 2 is perspective view of a universal tracker device of the present invention.

With specific reference to FIG. 2, the universal tracker device 200 includes a plurality of infrared light emitting diodes 202, a communication transceiver 204, and a status light 206. In the preferred embodiment, the universal tracker device 200 includes first, second, third, fourth and fifth light emitting diodes 202a,202b,202c,202d,202e.

The tracker 200 also contains a battery holder 208 for holding a battery (not shown). The battery of the tracker 200 and the other smart instruments 102 is preferably a common lithium battery that is pre-sterilized that is to be loaded into the battery holder 208 just prior to use and is not to be re-sterilized.

The status light 206 glows in a green color for approximately three seconds after placement of the battery into the battery holder 208 indicating that the tracker 200 is energized and has passed a series of self diagnostic test. Once the tracker 200 is energized the tracker is attached to the clamp 258 by a zero tolerance adapter interface 210 and a release button 212. The tracker is then ready to be initialized by depression of an activation button 214. The tracker 200 also contains a validation point 216 for validating other smart instruments 102.

Figure 3:
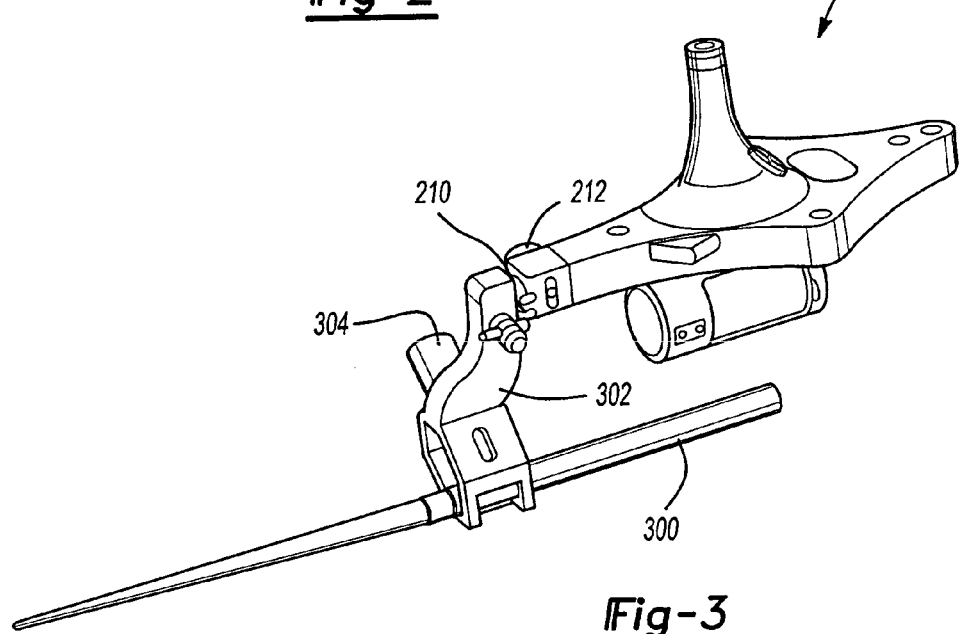
FIG. 3 is a perspective view of the universal tracker device adapted to a general instrument.

With specific reference to FIG. 3, a universal tracker device 200 is shown adapted to be used with a general instrument 300, shown as a pointer. Any number of common surgical instruments may be tracked with the invention by attachment to the universal tracker device 200, including but not limited to a probe, scalpel, suction device, pin, or clamp. In order to couple the tracker device 200 to the general instrument 300, an adapter 302 is connected to the adapter interface 210 of the universal tracker device 200 and the general instrument 300 is attached by a clamp screw 304. During use, the universal tracker serves as a communication device between the attached instrument 300 and the sensor array 104.

With reference to FIG. 4, an assembly view of a universal tracker device 200 is shown. The tracker 200 consists generally of a housing 402, a PC board assembly 404, a cover plate 406, and a battery housing 408 interconnected by a plurality of fasteners 410. The plurality of infrared light emitting diodes 202 are recessed into a plurality of LED apertures 412,412a,412b,412c,412d,412e in the housing 402 and are held in place by a plurality of epoxy rings 414, 414a,414b, 414c,414d,414e. A plurality of electrical leads 416 connect the diodes 202 to the PC board assembly 404.

The tracker 200 activation button 214 is biased in the housing 402 by a compression spring 418 and contains a magnet 420.

The communication transceiver 204 includes of an IR window 422 and a gasket 424. The gasket 424 serves to seal the IR window 422 when installed in the housing 402.

The status light 206 is recessed through a status light aperture 426 and is connected to the PC board assembly 404 by an electrical lead 428. A gasket 430 forms a seal.

Attached to the PC board assembly 404 is a hall effect switch 432. The battery housing 408 is attached to the cover plate 406 and contains a positive battery contact spring 434, a negative battery contact spring 436, and a removable cap 43 for placement of a battery (not shown) into the battery housing 408.

When the universal tracker device 200 is used as part of the patient tracking system 502, a magnet (not shown) triggers another hall effect switch (not shown). When the universal tracker device 200 is activated (see below), the status of the hall effect switch is sent to the system 100. This allows the system 100 to distinguish between a universal tracker device 200 being used as part of a patient tracker system 502 or a universal tracker device 200 with a generic instrument 300. A magnet may also be used for functional differentiation, e.g., a device tracker is adapted to sense the present of the magnet to determine if it is being used as part of a patient tracker system 502 or a universal tracker device 200 with a generic instrument 300.

A status of the universal tracker device battery and the diodes 202 may be displayed on the monitor 108. The status feature is present in all of the smart instruments of the present invention. The PC board of the universal tracker 200, and all of the smart instruments 102, contain a non-volatile memory circuit (not shown) that allows the instruments to store information about the instrument such as a unique ID number, and calibration information in the instrument itself. Storing calibration information in the instrument 102 allows the instrument 102 to be re-calibrated in a surgical field setting. The memory circuit of the instruments 102 such as the tracker 200 contain updateable memory (not shown) that can be updated or changed at any time. This feature improves the life of the smart instruments 102 such as the tracker device 200 by allowing the tracker device 200 to be updated with an improved software package as the image-guided system 100 changes over time. An ability to update over time improves the life of the tracker device 200 and reduces a lifetime cost of the image-guided surgery system 100. The EE memory along with the microprocessor based circuitry of the instruments such as the tracker 200 also allows the sensor array 104 and computer system 106 to immediately detect a new instrument entering the surgical field without requiring the operator 120 to load a new software program onto the computer system 106 prior to using the new instrument 102.

The properties of the smart instruments 102, such as geometry and functional features, are preferably graphically displayed on the computer monitor 108 to enable visual display of their spatial and functional relationships to other smart instruments, surgical equipment, and the surgical field.

The smart instrument may also store the specific geometry of the active part of the smart tool, i.e., the tip or the part of the tool that is in contact with the patient or delivering some kind of energy, mechanical, electrical, sonic, electromagnetic, etc . . . , to alter the patient's tissues. The geometry of the active part of the smart instrument is preferably stored in memory.

With reference to FIGS. 6-8, a smart instrument 102 in the form of a specially adapted or specific purpose instrument will now be discussed in detail. For exemplary purposes only, the smart instrument 102 is shown as a pointer instrument 600.

The pointer instrument 600 has a housing 602 constructed of a metallic material and shaped in an ergonomic design to be held in the operator's hand. The pointer instrument 600 has a plurality of infrared light emitting diodes 604 and a communication transceiver 606 for communicating with the sensor system 104. The pointer instrument 600 or any smart instrument 102 may include multiple transceivers to allow the instrument to be used in any direction. A smart instrument 102 may have any number of light emitting diodes 604 depending upon the nature of the smart instrument and the resolution or degree of accuracy required for its position. The pointer instrument 600 illustrated has first, second, third and fourth light emitting diodes 604a,604b,604c,604d.

The control buttons 114 of the pointer instrument 600 include an up button 608, a select button 610, and the down button 612 for remotely controlling the computer system 104 from the smart instrument 102.

The function of the buttons 608, 610, 612 may be specifically configured to suit a specific operator 120. For example, the up button 608 and the down button 612 are generally configured to navigate (up and down or left to right) through the software running on the computer system 104, i.e., to navigate through the options available at the current operation state. The select button 610 button generally is used to actuate a current selection. However, depending on a particular operator's preference, the buttons can be reprogrammed, e.g., to interchange the functions of the up and down buttons 608, 612.

Controlling the computer system 104 from the instrument 102 allows the operator 120 to remain in a surgical field to make adjustments to the computer system 104 thereby improving the efficiency of an operation.

The pointer instrument 600 also contains a work tip shown as a pointer 614, a status light 616, and a battery holder 618. The status light 616 blinks every few seconds to indicate normal operation of the instrument 600.

With specific reference to FIG. 7, a partial assembly view of the pointer instrument 600 is shown. The pointer instrument 600 includes the housing 602, a battery housing 702, and a base assembly 704 interconnected by a plurality of fasteners 706. The up button 608, the select button 610, and the down button 612 are mounted in an associated aperture 708,710,712 respectively, in the housing 602 by a plurality of threaded pins 714a,714b and compression springs 716a, 716b,716c. Mounted under each button 608,610,612 is a plurality of magnet carriers 718a,718b,718c and magnets 720a, 720b,720c. The magnets 720a,720b,720c and the springs 716a,716b,716c allow the buttons 608,610,612 to toggle around the pins 714a,714b.

Under the buttons 608,610,612 is a foam pad 722 to insure accurate positioning of the hall sensors relative to the buttons 608,610,612. The battery housing 702 is mounted in a channel 724 located in the base assembly 704. The battery housing 702 contains a positive and negative battery contact spring 726, 728 and a cap 730 for holding a battery (not shown).

With specific reference to FIG. 8, another partial assembly view of the pointer instrument 600 is shown. The pointer instrument 600 includes a cover plate 802 connected to the PC board assembly 804 by fasteners 706.

The light emitting diodes 604a,604b,604c,604d are mounted into the housing 602 with a plurality of epoxy rings 806 and are connected to the PC board assembly 8043 by a plurality of leads 808. The status light 616 is similarly mounted into the housing 602 with an epoxy ring 810 and is connected to the PC board assembly 804 by lead 812. The communication transceiver 606 has an IR window 814 mounted to the housing 602 with a gasket 816 and a pair of fasteners 706 and spacers 818. The PC board assembly 804 is connected to the battery (not shown) by a pair of battery leads 820.

Figure 9:
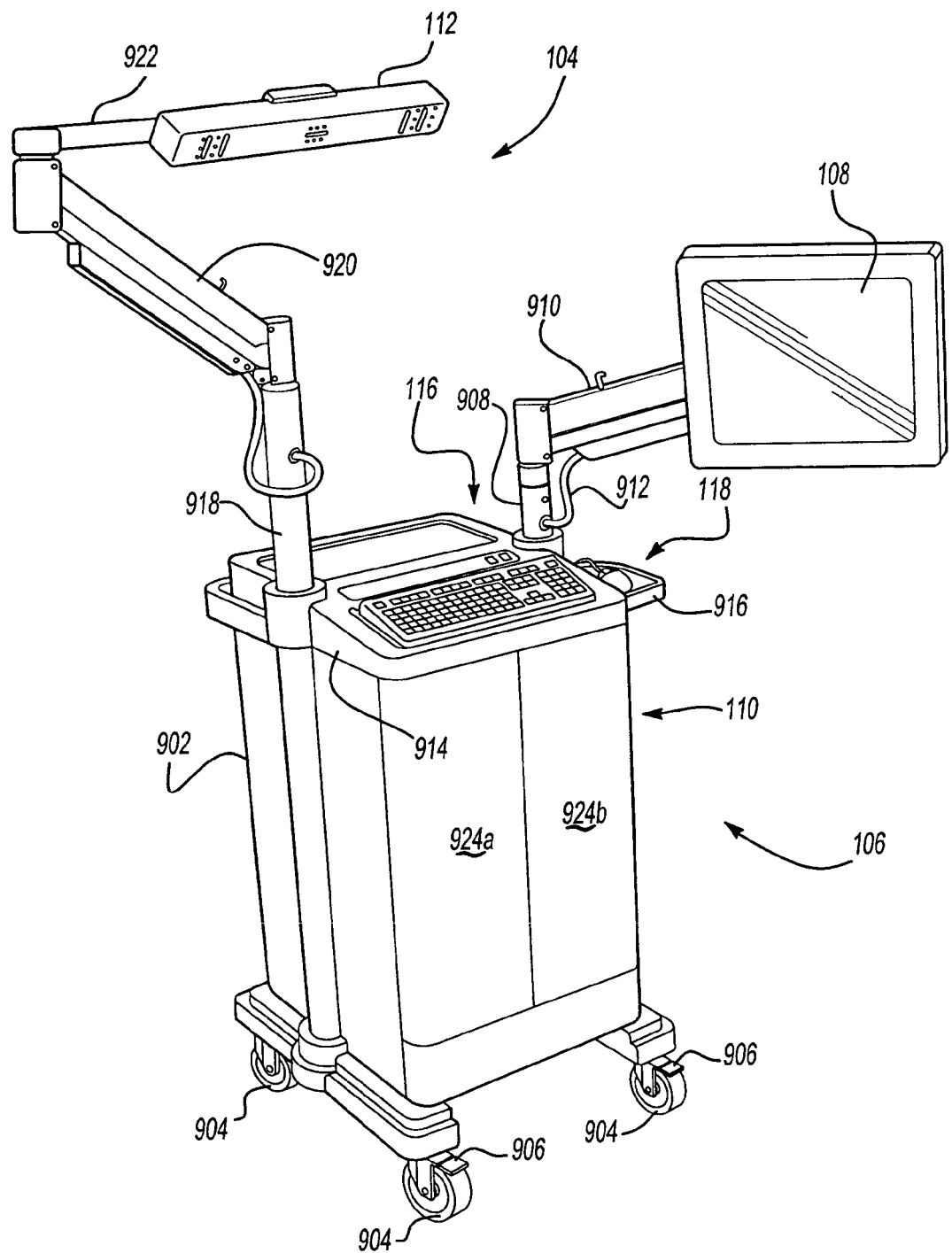
FIG. 9 is a perspective view of a computer cart assembly of the present invention.

With reference to FIG. 9, a computer cart assembly 110 of the invention according to an embodiment of the present invention is shown. The computer cart assembly 110 consists of a cabinet 902 mounted on four wheels 904 (only three are shown) with four corresponding wheel locks 906 for activation to prevent the cart assembly 110 from moving unintentionally. Mounted to the cabinet 902 by a monitor extension post 908 and a pivotable monitor extension arm 910 is the monitor 108. The monitor 108 of the preferred invention is a flat panel high resolution monitor. The monitor 108 is connected to the computer system 106 by a monitor cable 912 that is routed along the monitor extension arm 910 and through the monitor extension post 908. Mounted on the cabinet 902 is a keyboard tray 914 and a mouse tray 916 for holding the keyboard 116 and the mouse 118, respectively.

The sensor array 112 is mounted to the cabinet 902 by a sensor array extension post 918, a pivotable vertical sensor array extension arm 920, and a pivotable horizontal sensor array extension arm 922.

The cabinet 902 includes first and second front cabinet doors 924a,924b.

Figure 10:
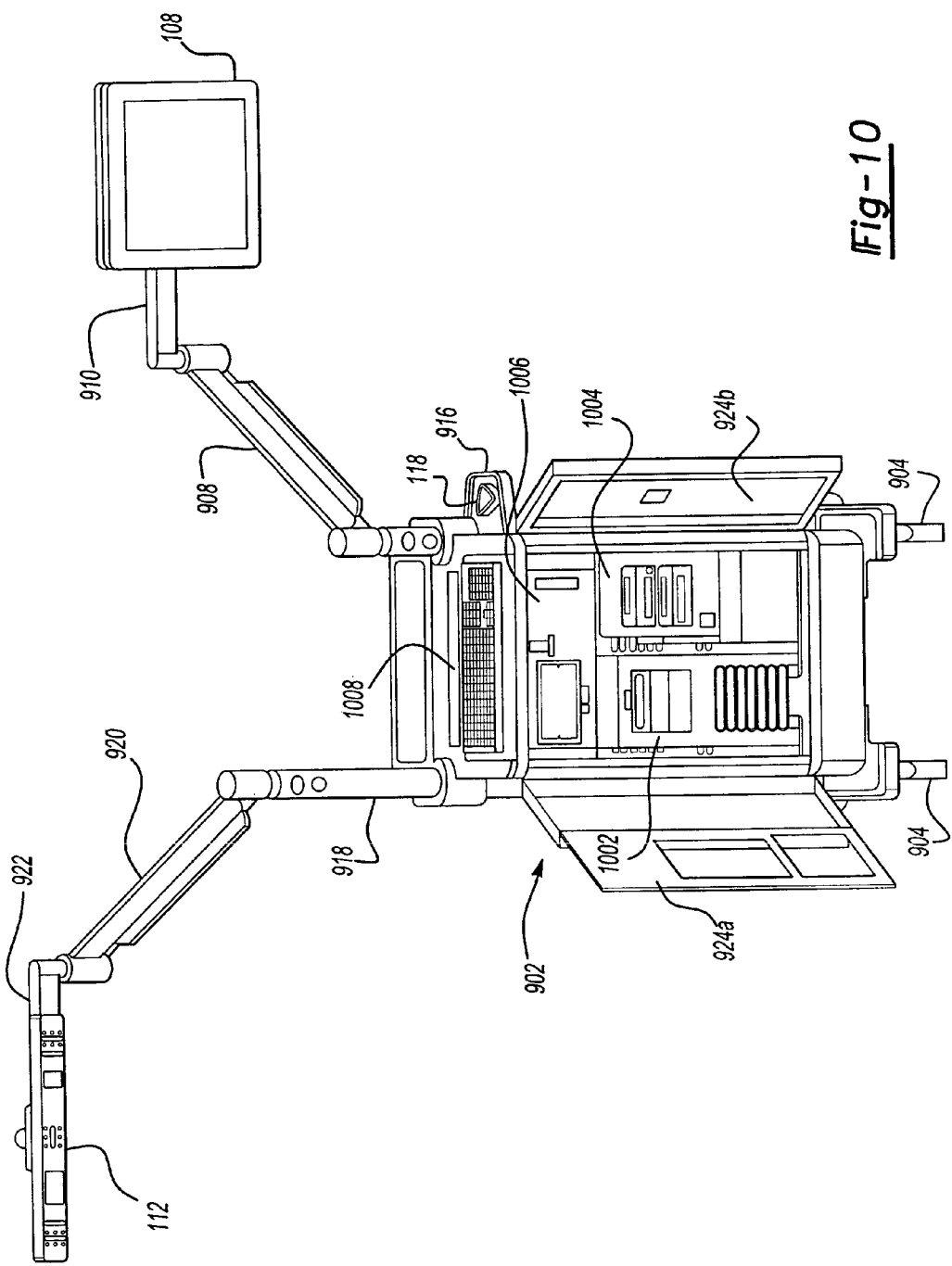
FIG. 10 is a partial assembly front view of the computer cart assembly of FIG. 9.

With reference to FIG. 10, the computer cart assembly 110 is shown with front cabinet doors 924a,924b in an open position. The front cabinet doors 924a,924b expose a computer workstation assembly 1002, a disk bay and storage assembly 1004, and a localizer 1006. A switch panel assembly 1008 is also shown mounted within the keyboard tray 914.

Figure 11:
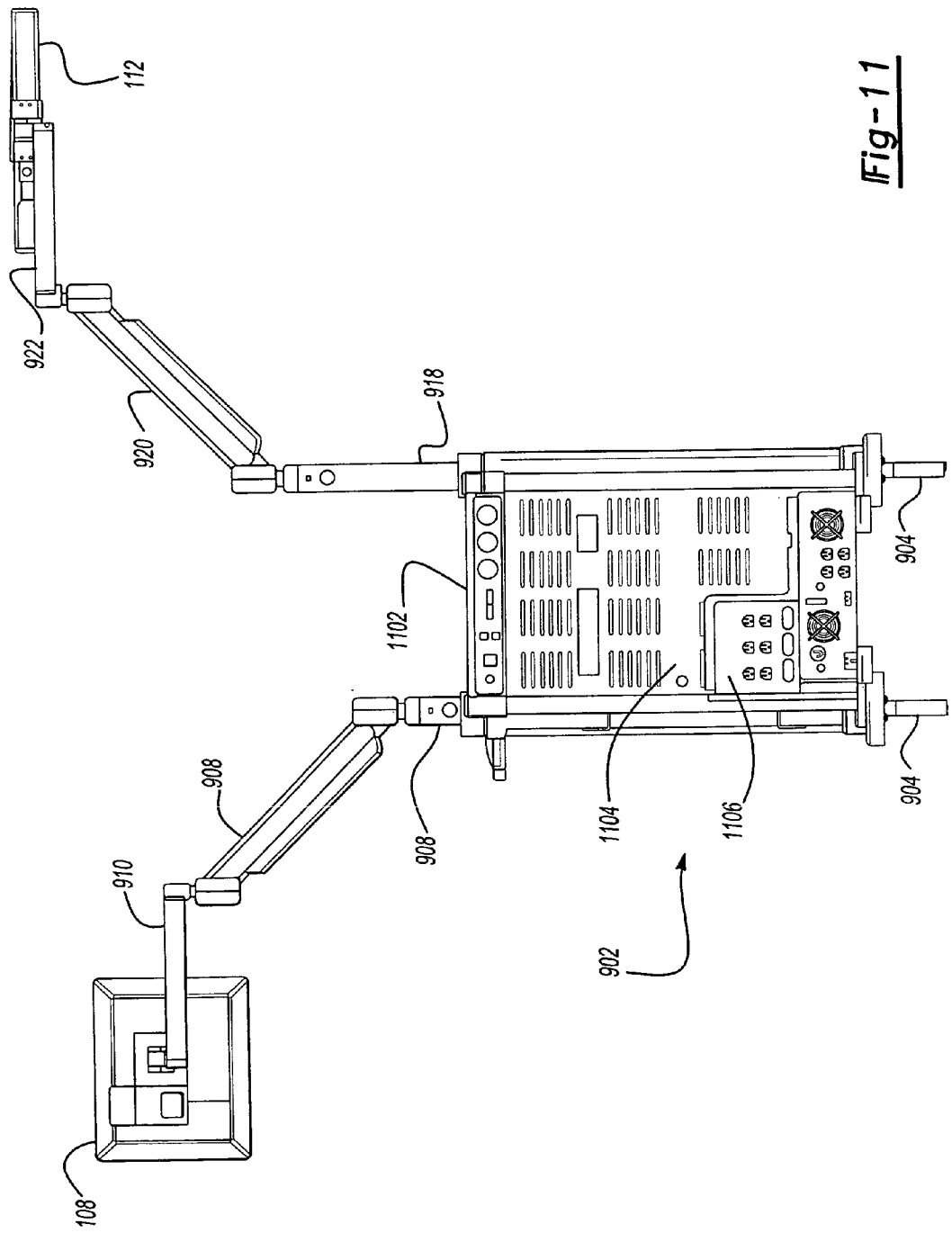
FIG. 11 is a rear perspective view of the computer cart assembly of FIG. 9.

With reference to FIG. 11 a rear view of the computer cart assembly 110 is shown. Mounted on the rear of the cart assembly 110 is a rear panel assembly 1102, a cover 1104, and a switch box assembly 1106.

Returning to FIG. 12, an assembly view of the sensor array 112 is shown. The sensor array 112 is connected by a plurality of fasteners 1206 to a mounting plate 1208 and a universal mount 1210. The universal mount 1210 connects the sensor array 112 to the sensor array horizontal extension arm 922.

As discussed above, the sensor array 112 includes a plurality of position sensors 1202 and a plurality of transceivers 1204. In the preferred embodiment, the plurality of sensors are cameras able to detect infrared light and the transceiver 1204 communicate using infrared light. Alternatively, the infrared transceivers 1204 could be RF transceivers.

The position sensors 1202 contain their own calibration information allowing the localizer 1006 to be placed away from the sensor array 112 in the computer cart assembly 902. The sensor array 112 establishes a detection field whereby the signals from the smart instruments 102 are received by the sensor array 112. In order to function properly, the smart instruments 102 must be placed within the detection field in order for the computer system 106 to recognize the position of the smart instruments 102.

Figure 13:
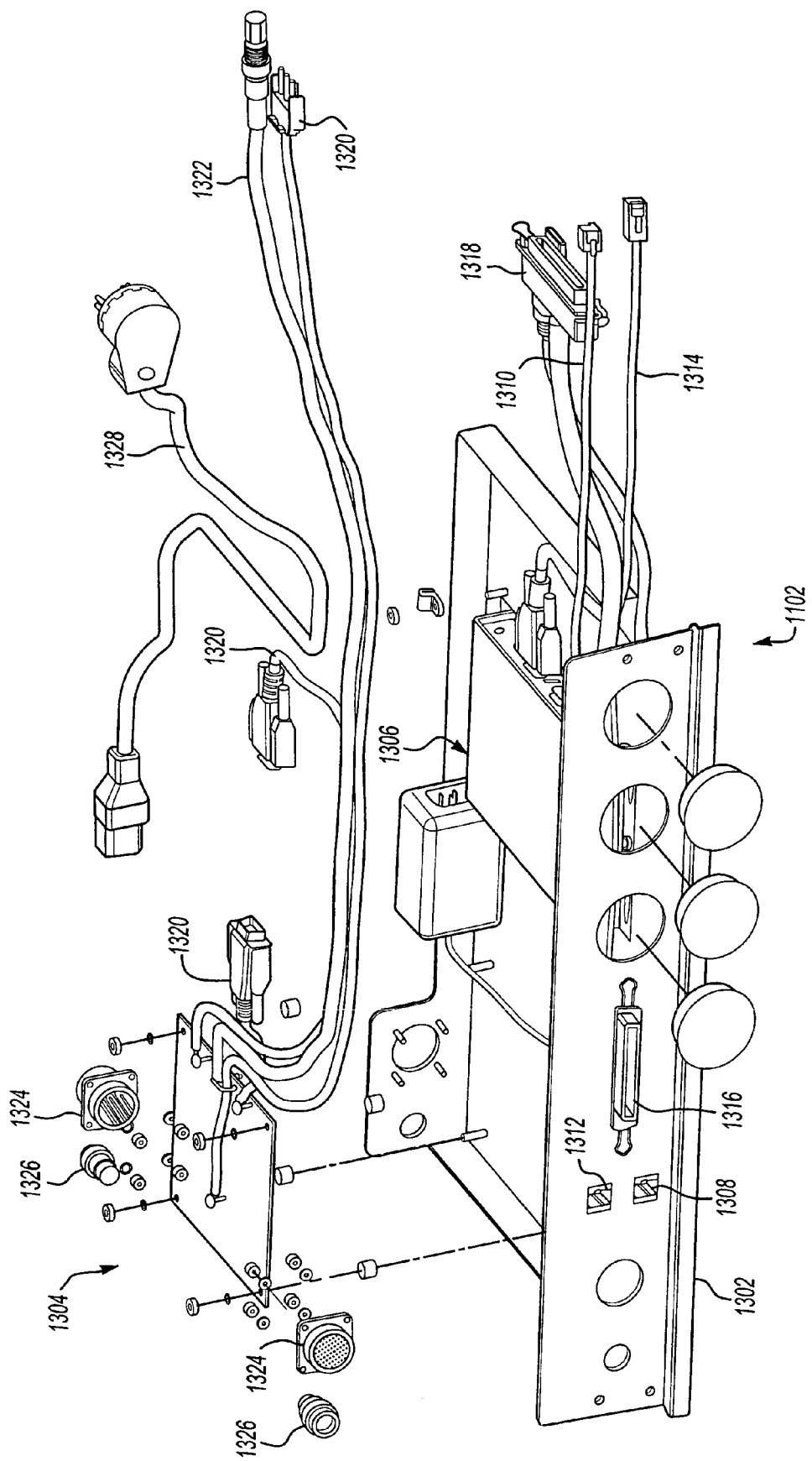
FIG. 13 is assembly view of a rear panel assembly of the present invention.

With reference to FIG. 13 an assembly view of the rear panel assembly 1102 is shown. The panel assembly 1102 consists of a housing 1302 for mounting of a monitor interface assembly 1304 and a video amplifier 1306 and coordinating a plurality of associated cables, cords, and plugs (as described below). The panel assembly 1102 includes an external modem port 1308 connected to a phone cable 1310, a data port 1312 connected to a patch cable 1314, and a SCSI port 1316 connected to a SCSI cable 1318. The panel assembly 1102 also contains a plurality of communication cables 1320 and a video cable 1322 that are routed through the panel assembly 1102 and connected to the monitor interface assembly 1304. The monitor interface assembly 1304 contains a monitor cable plug 1324 and a sensor array plug 1326. The panel assembly 1102 also includes a power cord 1328.

Figure 14:
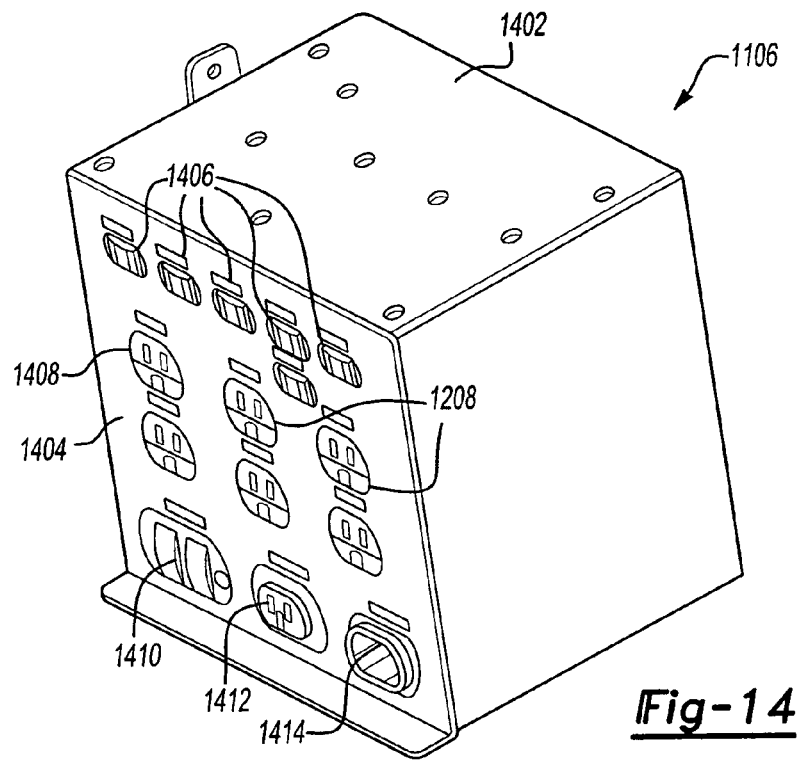
FIG. 14 is a perspective view of a switch box assembly of the present invention.

With reference to FIG. 14, the switch box assembly 1106 is shown. The switch box assembly 1106 contains a top 1402 and a front panel 1404 that contains a plurality of communication ports 1406, a plurality of medical grade outlets 1408, a fused power entry module 1410, an AC power outlet module 1412, and an AC power entry module 1414. The switch box assembly 1106 and the panel assembly 1104 allow for a connection of a computer network, a telephone line, a plurality of microscopes, and a plurality of other operating room equipment (not shown).

Figure 15:
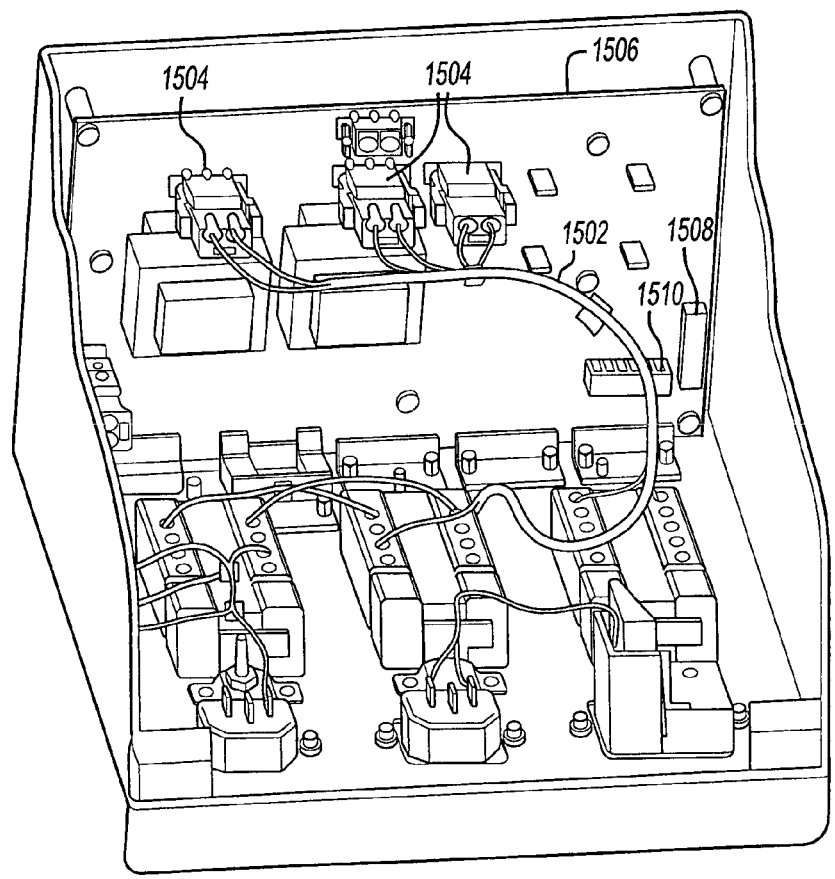
FIG. 15 is a partial assembly view of the switch box assembly of the present invention.

With reference to FIG. 15, the switch box assembly 1106 is shown with a back and a side panel (not shown) removed. The fused power entry module 1410, the AC power outlet module 1412, and the AC power entry module 1414 are shown interconnected to each other and to the plurality of outlets 1408 by a plurality of wires 1502. The plurality of outlets 1408 are connected to a plurality of universal in-line plugs 1504 by the of wires 230. Mounted to the top 1402 is a cart power control assembly 1506 that houses the universal in-line plugs 1504. Also housed on the cart power control assembly 1506 is an image guided cart UPS micro 1508 and an image guided cart switch interface micro 1510. The micro internal to the switch box allow for easy power up and power down of the complete system. A single push of the on button will turn the system on and pushing the standby button will turn the system off. During turn off, the micros synchronizes the Windows operating system shutdown and power to eliminate system crashes.

Any number of smart instruments 102 may be active at any one time. The surgery system 100 operates on a scanning cycle which has a length determined by the number of smart instruments 102 (including universal tracker devices 200) being tracked. In the preferred embodiment, the image guided surgery system 100 only tracks the location of the smart instrument 102 currently being used by the operator 120 and any active universal tracker device 200 (see below).

As described below, the system 100 displays a computer graphic on the monitor 108 representing the patient 122 or a portion of the patient's body. The graphic can be a two-dimensional, three-dimensional or multi-planer, e.g., a picture, x-rays, an MRO image, outline, line drawing or any other representation of the patient 122. The computer system 106 receives information from the sensor system 104 regarding an active smart instrument's position and matches up this position with the graphic representing the patient 122. In one embodiment, the system 100 displays a line on the monitor 108 representing the active smart instrument 102. In another embodiment, the system 100 displays a graphic depicting the active smart instrument 102.

With reference to FIG. 16, activation of a new smart instrument 102 will now be discussed. In a first process block 1602, a new smart instrument 102 is placed in a ready to be activated state. When a smart instrument 102 is powered up, i.e., by insertion of the battery, it is in a ready to be activated state. In a second process block 1602, the operator 120 actuates the activation button 214 or the select button 610 so that the image guided surgery system 100 recognizes the smart instrument 102.

Each smart instrument 102 has a unique serial number. With reference to FIG. 17 in the preferred embodiment, the activation of a new smart instrument 102 may occur at the beginning of each scan cycle. In a third process block 1702, the surgery system 100 generates a request for any new tool to identify itself. Preferably, the computer system 106 (through the transceivers 1204a,1204b) generates a New Tool Inquiry Package Signal. The New Tool Inquiry Package Signal includes a serial number identification for a target tool 102 and a request for the tool's serial number. The serial number identification for a target tool is set to a default value, e.g., zero (0). Only smart instruments 102 that are in the ready to be activated state and whose activation button 214 is actuated respond to a request to smart instruments having a serial number equal to the default value.

If a fourth process block 1704, if no response is received to the New Tool Inquiry Package Signal within a predetermined time period, then the system 100 continues with its normal scans in the fifth process block 1706.

In a sixth process block 1706, if a new smart instrument 102 is ready to be activated, the smart instrument 102 responds to the New Tool Inquiry Package Signal and the system 100 stops the scanning.

In a seventh process block 1708, the new smart instrument 102 and the computer system 104 then communicate back and forth to relay the information the computer system 104 requires in order to initial the new smart instrument 102 to add it to the scanning process. After this process is done, then control proceeds to the normal scanning cycle in the fifth process block 1706.

The above process must be completed for each smart instrument 102 to be used during the procedure. Typically, each smart instrument 102 to be used is initialized prior to the start of the procedure. However, new tools 102 may be added at any time.

The following is a list of the data that may be stored within the smart instruments 102. Some or all of this data may be transmitted to the computer system 106 during the initialization process (see above).

Serial Number: This is the unique electronic serial number for the smart instrument 102 that is used to identify the smart instrument 102 to the system 100.

Model Number: This is the model number of the smart instrument 102. The computer system 106 may utilize this information to retrieve information regarding the smart instrument 102 stored on the computer system 106 such as a graphic to be displayed on the monitor 108 while the smart instrument 102 is being used.

Instrument Name: This is the name of the smart instrument 102. The Instrument Name is typically displayed on the monitor 108 while the smart instrument 102 is being used.

Generic Tool Information: This is the generic type of the smart instrument 102. The computer system 106 utilizes this information to create graphics and other instrument parameters if a model number match can not be found.

Generic Type: This is a generic type for the smart instrument Preferably the Generic Type is one of the following: unknown, navigation tool, calibration tool, tracker, keypad, frame based tool, functional tool.

Tip Type: This is the type of tip on the instrument. Type of tips include: cylinder, sphere, cone, truncated cone, and blade.

Minimum LEDs: This is the minimum number of LEDs that must be seen by the sensor system 104 for the smart instrument 102 to be recognized.

Dimensional Data: The Dimensional Data represents the physical size of the smart instrument 102 and may include a radius, a bottom radius, a bottom width, a length, a top radius, a top width, and a thickness.

Number of LEDs: This is the total number of infrared light emitting diodes on the smart instrument 102.

LED on Time: This is the amount of time that an infrared LED is activated.

Tip Position: This is the position of the smart instrument's tip in relation to the instrument's coordinate system. Preferably, the Tip Position includes an X, Y, Z, yaw, pitch, and roll value.

Tip Correction: Tip Correction represents a correction factor for the position of the tip as a result of manufacturing tolerances and/or tip displacement.

Button Parameters: The Button Parameters define the buttons present on a smart instrument 102. The Button Parameters may include the number of buttons, a clock delay, and a button timeout.

Number of Calibration Points: This is the number of calibration points on a smart instrument 102.

EERAM Revision: This is the revision level for the information stored on the RMS Match: This is the parameters used to calculate the match of the instrument LEDs.

LED Position: This parameter contains the position of a LED in relation to the smart instrument's coordinate system. Typically, there will be an LED position for each LED contained on an smart instrument 102. Preferably, the LED Position includes an X, Y, Z, and a X, Y, and Z component of a normal vector.

Button Function: This parameter defines the function of a button on the smart instrument 102.

Calibration Point: The position of the smart instrument's calibration point in relation to the instrument's coordinate system. Preferably, the Calibration Point includes an X, Y, X and radius value.

With reference to FIG. 18, operation of the universal tracker device 200 as a component in the dynamic reference frame and validation of another smart instrument 102 using the universal tracker device 200 will now be explained.

In an eighth process block 1802, the universal tracker device 200 is coupled to the patient tracking system 502. The universal tracker device 200 must be positioned to ensure optimal alignment of the light emitting diodes 202 with the sensor array 104. The universal tracker device 200 must also be positioned within a working volume of the system 100. There should be no obstacles that interrupt the infrared beams between the universal tracker 200 and the sensor array 112. Furthermore, the universal tracker 200 should be positioned to give complete access to the surgical site.

Figure 19:
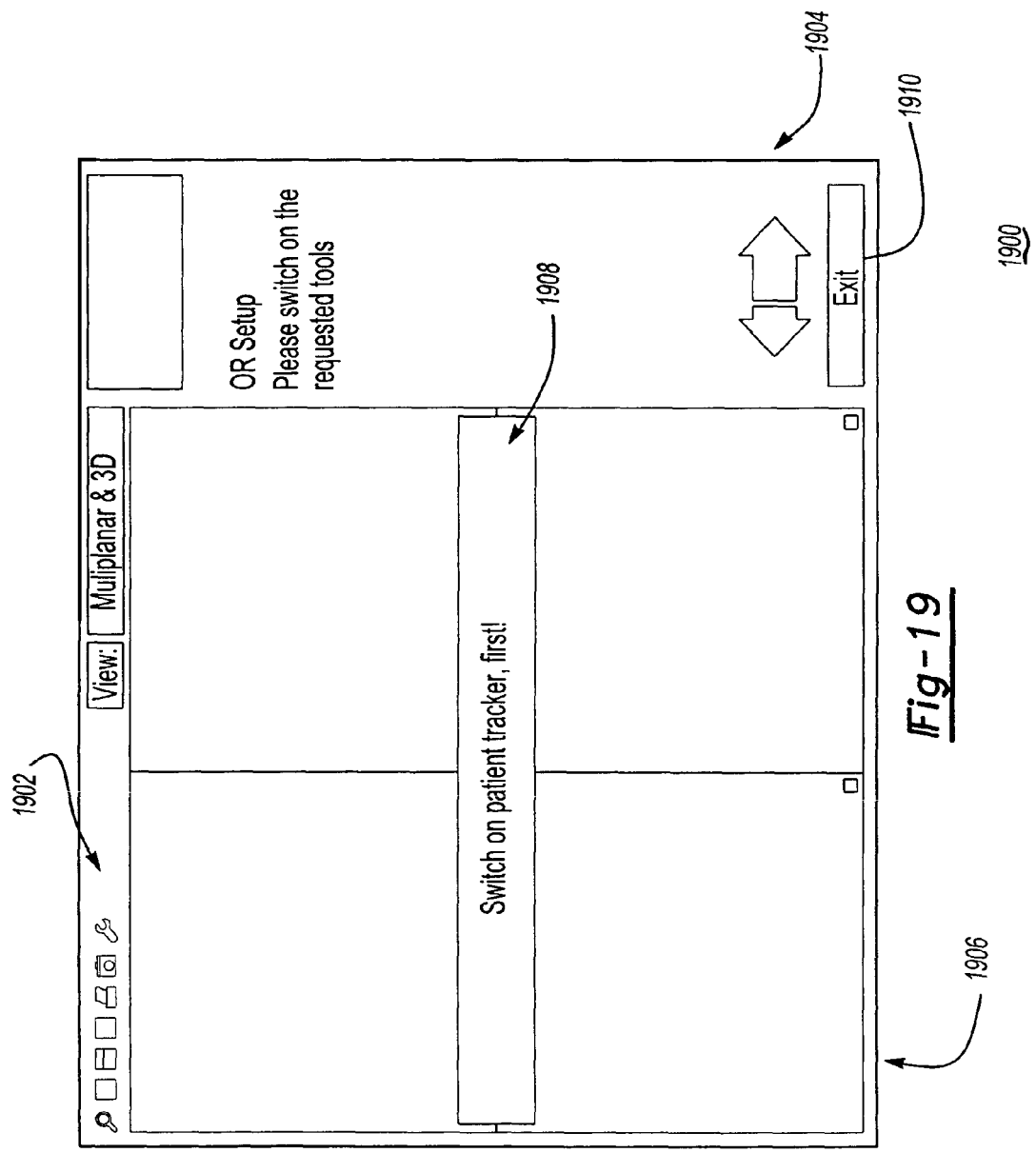
FIG. 19 is a diagrammatic illustration of a display screen with an initial banner, according to an embodiment of the present invention.

At this point, the computer system 106 must also be initialized. With reference to FIG. 19, the computer system 106 displays a display screen 1900 on the monitor 108. The display screen 1900 includes a button bar 1902, an information section 1904 and a display section 1906. In the preferred embodiment, when the computer system 106 is initialized, a banner 1908 instructing the operator 120 to activate the tracking device 200 is displayed.

Figure 20:
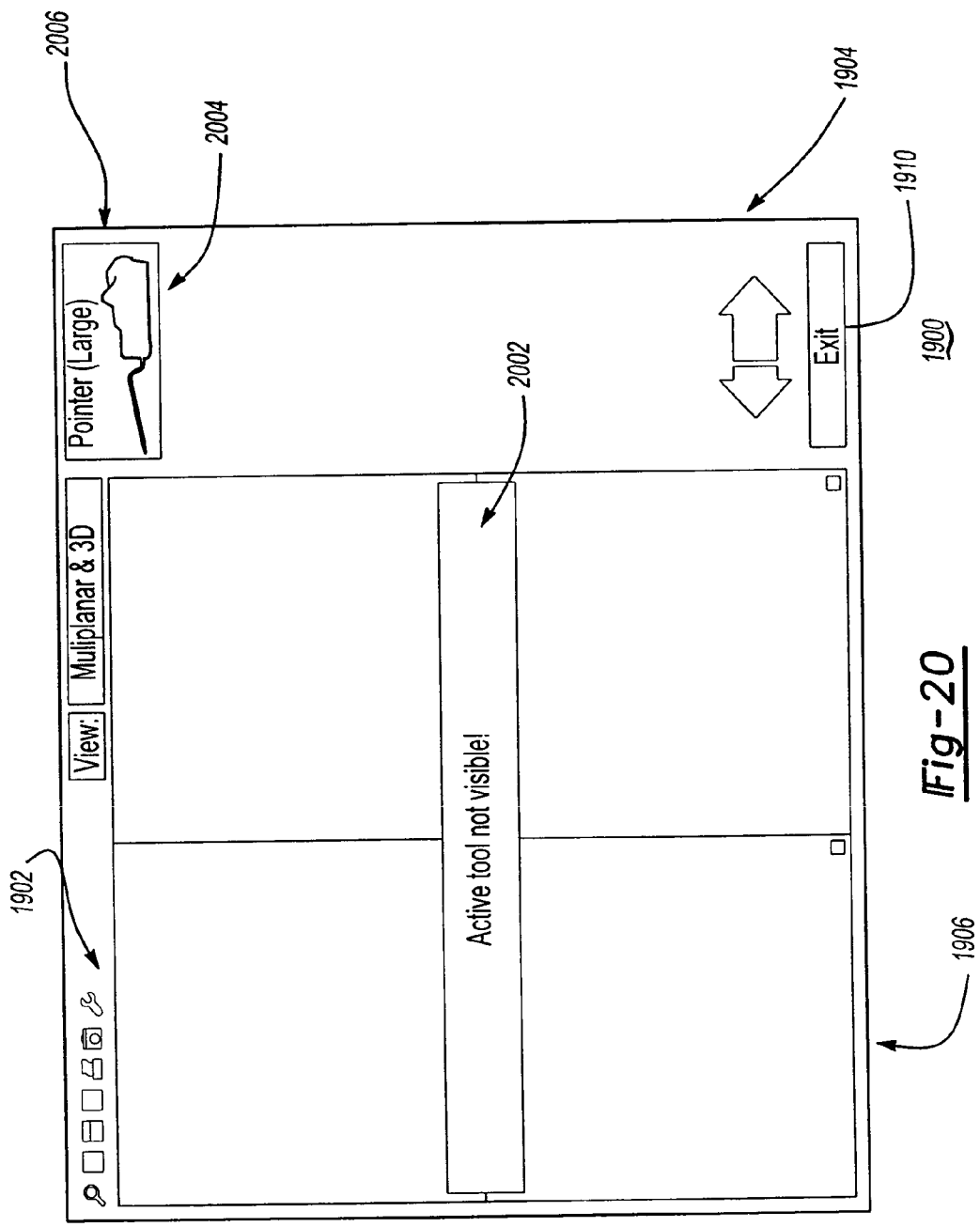
FIG. 20 is a diagrammatic illustration of the display screen of FIG. 19 with a second banner.

In a ninth process block 1804, once the universal tracker 200 is in position the operator 120 momentarily depresses the activation button 214, as described above, to activate the universal tracker 200. With reference to FIG. 20, once the universal tracker device 200 has been activated a banner 2002 is displayed indicating that no active tool is visible to the system.

In a tenth process block 1806, a smart instrument 102 must be activated. Returning to FIG. 20, once the smart instrument 102 has been activated, a graphic or pictogram 2004 of the smart instrument 102 (based on the Serial number, Model Number, Generic Tool Information or Generic Type) and the Name of the smart instrument 102 is displayed in the information section 1904 of the display screen 1900. Once the smart instrument 102 has been activated, the red banner 2002 will disappear.

Figure 21:
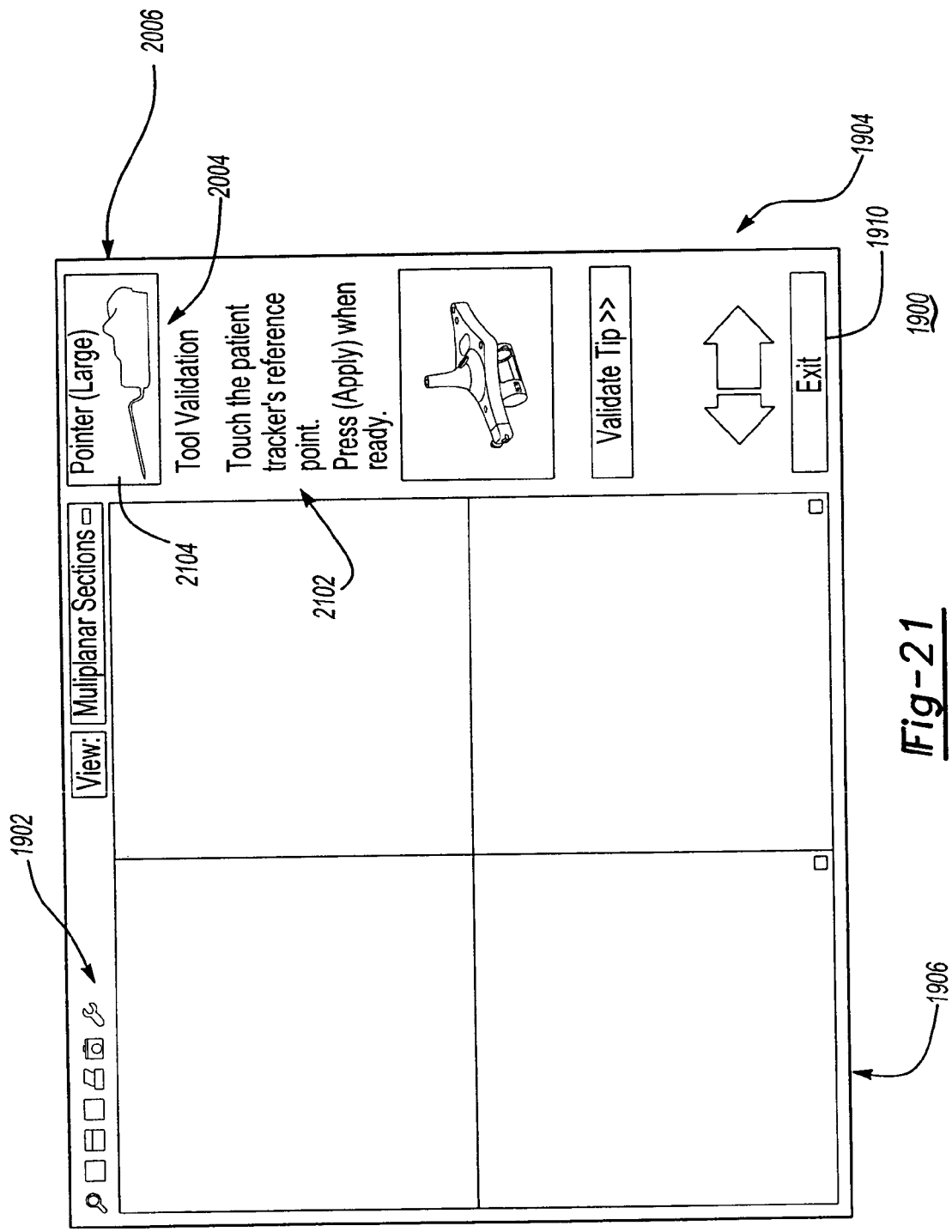
FIG. 21 is a diagrammatic illustration of the display screen of FIG. 19 with an information section having tool validation instructions.

After the smart instrument 102 has been activated, it must then be validated, i.e., its position relative to the patient tracker 502 must be verified. With reference to FIG. 21, instructions 2102 on the validation procedure are displayed in the information section 1904 of the display screen 1900. Furthermore, a background of the graphic 2004 is displayed in the color red to illustrate that the active tool 102 has not been validated.

Figure 22:
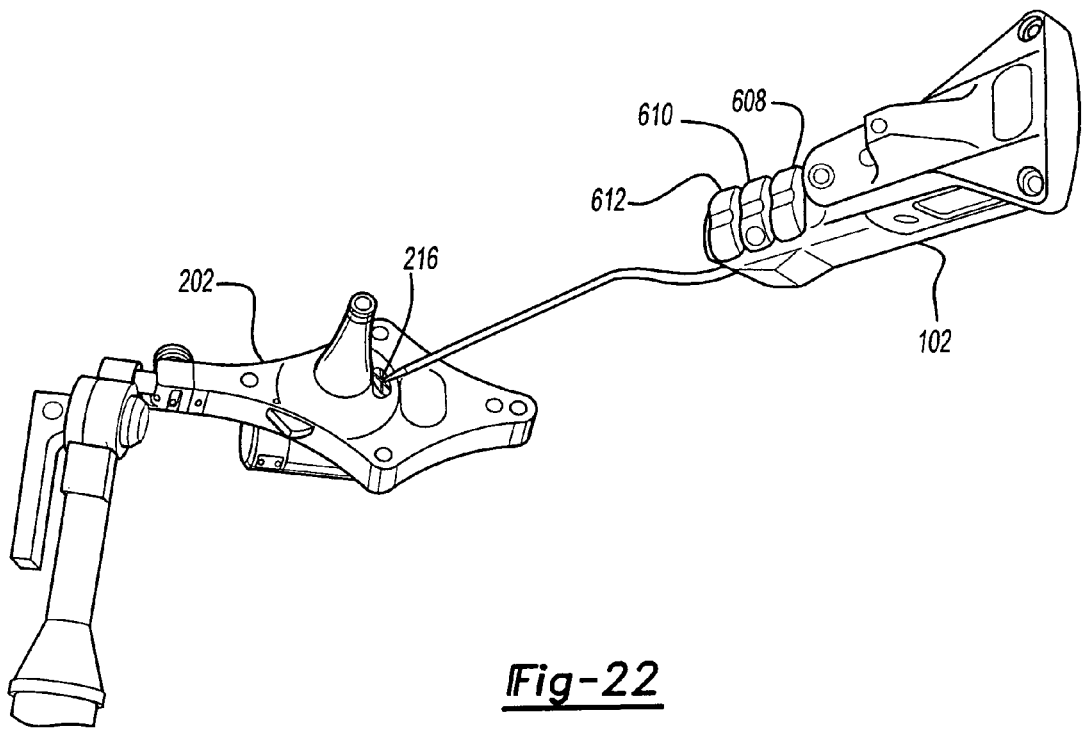
FIG. 22 is a perspective view of a universal tracker device and another smart instrument during a validation procedure.

With reference to FIG. 22, the smart instrument 102 is validated by placing the tip of the smart instrument 102 at the center of the validation point 216 of the tracker device 202 and actuating the select button 610. When the select button 610 is activated, the sensor system 104 detects the firing of the diodes 604 and transmits raw position information to the system computer 106.

In one embodiment, the localizer 1006 converts the raw position information into the position of the individual diodes 604 and transmits this information to the computer system 106. The computer system 106 utilizes this information to determine the position and orientation of the smart instrument 102. In another embodiment, the localizer 1006 converts the raw position information into the position and orientation information of the smart instrument 102 and/or computer system 106 and transmits this information to the computer system 106. The conversion of the raw position information by the localizer 1006 is well known in the art and is therefore not further discussed.

If the validation procedure is successful, the computer system 106 advances to the next step. Otherwise, the validation procedure may be redone through actuation of the select button 610 or the smart instrument 102 can be re-calibrated (see below).

Figure 24:
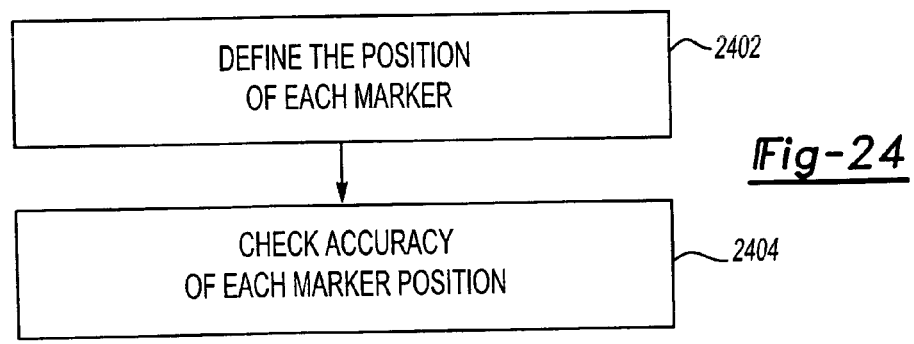
FIG. 24 is a flow diagram of a process for defining markers in a surgery system, according to an embodiment of the present invention.
Figure 23:
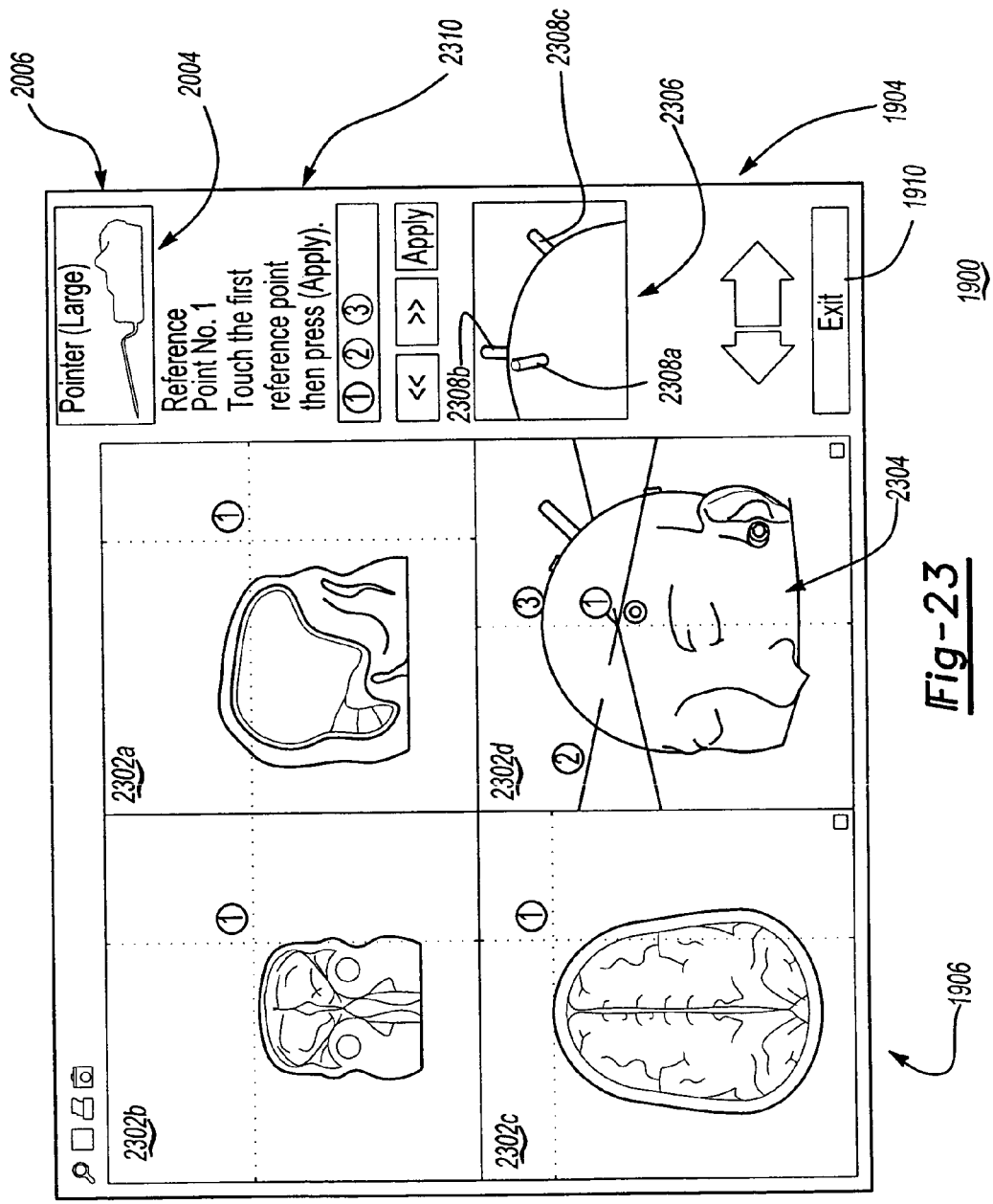
FIG. 23 is a diagrammatic illustration of the display screen of FIG. 19 during a point definition process.

With reference to FIGS. 23 and 24, the system 102 may utilize a plurality of markers 2308a,2308b,2308c,2308d located on a portion of the patient's body 122 in order to accurately register the surgical field relative to the graphic displayed in the display screen 1900. In an eleventh process block 2402, the position of each marker 2308a,2308b,2308c, 2308d is defined.

With specific reference to FIG. 23, the display section 1906 is divided into first, second, third, and fourth sub-sections 2302a,2302b,2302c,2302d. The first, second and third sub-sections 2302a,2302b,2302c contain MRI images of the patient's head. The fourth sub-section 2302d contains a computer image 2304 representing the head of the patient with the positions of the markers 2308a,2308b,2308c,2308d indicated.

In this example, there are three markers represented by the numbers 1, 2, and 3 in the fourth sub-section 2302d. The markers 2308a,2308b,2308c,2308d may be of several different types including sticker or screw-in posts. A graphic 2306 showing the screw-in post type or bone markers 2308a, 2308b,2308c is shown in the information section 1904. The graphic 2306 is for information purposes only and is not an actual picture of the patient 126.

Additionally, with reference to FIG. 33, a mesh or sheet 3302 made of a flexible material may be draped or placed over a portion of the patient 122. The mesh 3302 has a layer of light adhesive of one side and a plurality of markers 3304 on the other side. Preferably, the markers 3304 are spaced apart at known intervals. The mesh 3302 is stuck onto the patient 122 using the adhesive. The markers 3304 are thus visible by the localizer 1006 and can be used by the system 100 for surface matching as well as patient tracking.

In one embodiment, the markers 3304 are stickers which are used with a smart instrument 102 to register the positions of the markers 3304 within the system 102.

In another embodiment, the sheet 3302 is a smart instrument and the markers 3304 are light emitting diodes. Preferably, the position of the diodes is determined on the field. The diodes are connected to a breakout box and can be positioned using different means of attachment to any tissue of the patient, e.g., bone or skin. The geometry of the sheet 3302 can then be initialized to two modes: tracking of rigid tissues after determining the spatial relationships of the diodes with the sensor array. The second mode is to track soft tissue displacement or deformations over time. Using the first mode (tracking), the positional information of the sheet's diodes can be used to register the tracked feature of the patient to an image data set, e.g., a CT scan, using, for example, surface matching techniques. The computer system is adapted to determine the contour of the smart instrument and perform a surface matching operation with a known contour.

Returning to FIG. 23, the images contained in the sub-sections 2302a,2302b,2302c,232d are used to define the reference points represented by the markers 2308a,2308b,2308c in the system 100. A set of instructions 2310 are displayed in the information section 1904.

Additionally, light emitting diodes (not shown) may be fixedly attached to the markers 2308a,2308b,2308c for automatic registration of the marker positions in the system 100.

As shown by the graphic 2004, the active smart instrument 102 is a pointer. In order to define the position of the markers 2308a,2308b,230c within the system, the operator 120 places the tip of the pointer 102 on the marker and actuates the select button 610. The markers 2308a,2308b,2308c must be defined in the order instructed, i.e., 1, 2, 3. However, a marker 2308a, 2308b,2308c may be skipped altogether by scrolling through them using the control buttons 114.

The system 100 preferably allows the operator 120 to zoom and rotate the images in the display section 1906 to facilitate this process.

Returning to FIG. 24 in a twelfth process block 2404, after each marker 2308a,2308b,2308c has been defined in the system 100 the accuracy of the defined positions is checked. In the preferred embodiment, this is accomplished by calculating the relative agreement between the defined positions and known positions. If any of the defined positions differ from the expected position by over a predetermined threshold, then the marker position must be re-defined. In the preferred embodiment, the predetermined threshold is one (1) millimeter (mm) for skin markers and two and ½ (2.5) millimeters for the bone markers. However, these values may be adjusted.

Figure 25:
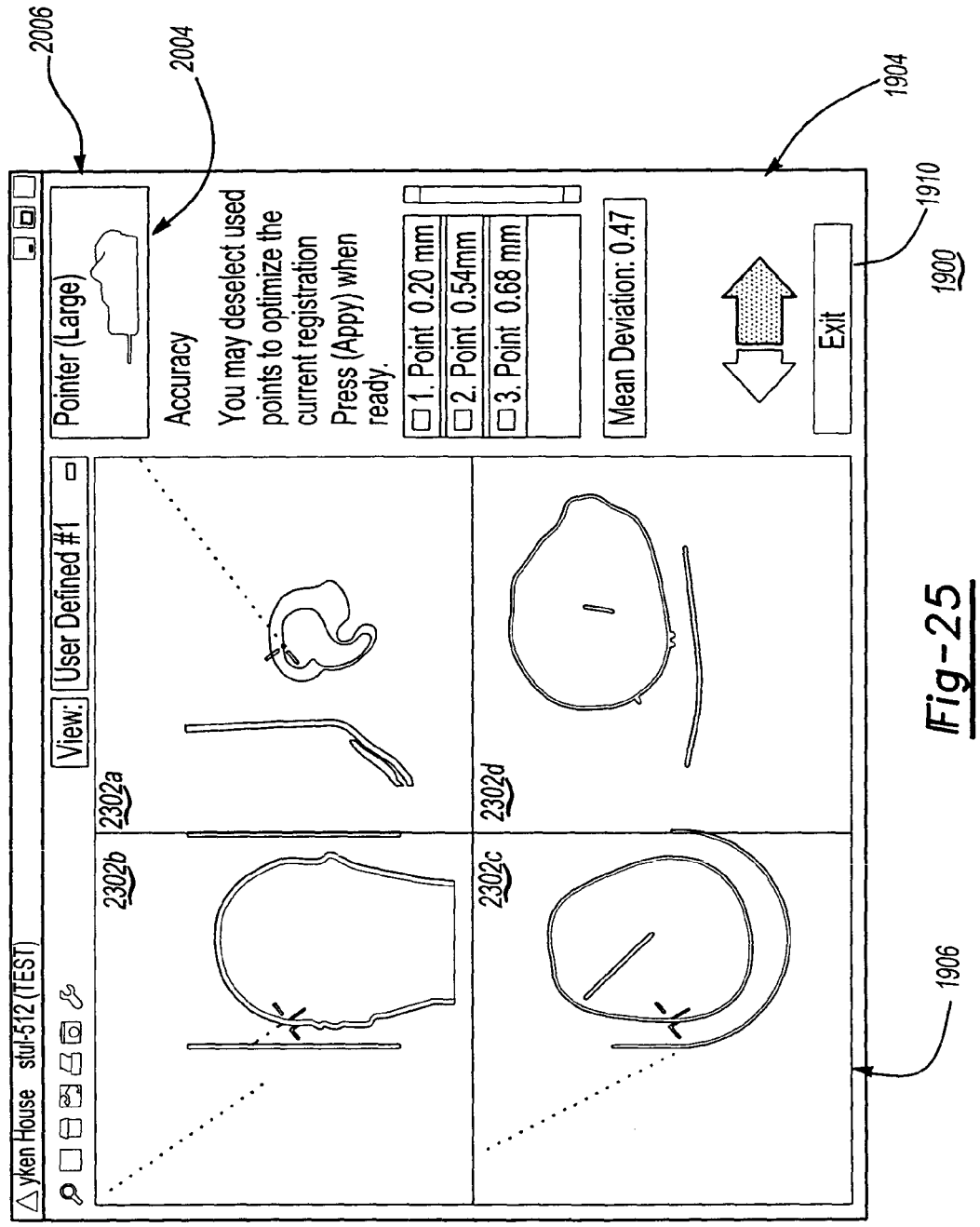
FIG. 25 is a diagrammatic illustration of the display screen of FIG. 19 with point definition accuracy information.

With reference to FIG. 25, the display screen 1900 showing the calculated accuracy is shown. The points represented by the markers 2308a,2308b,230c and their deviation are listed in the information section 1904. Even if a defined point is within the predetermined deviation, the system 100 allows the operator 120 to re-define the point to optimize the accuracy of the system 100.

Figure 26:
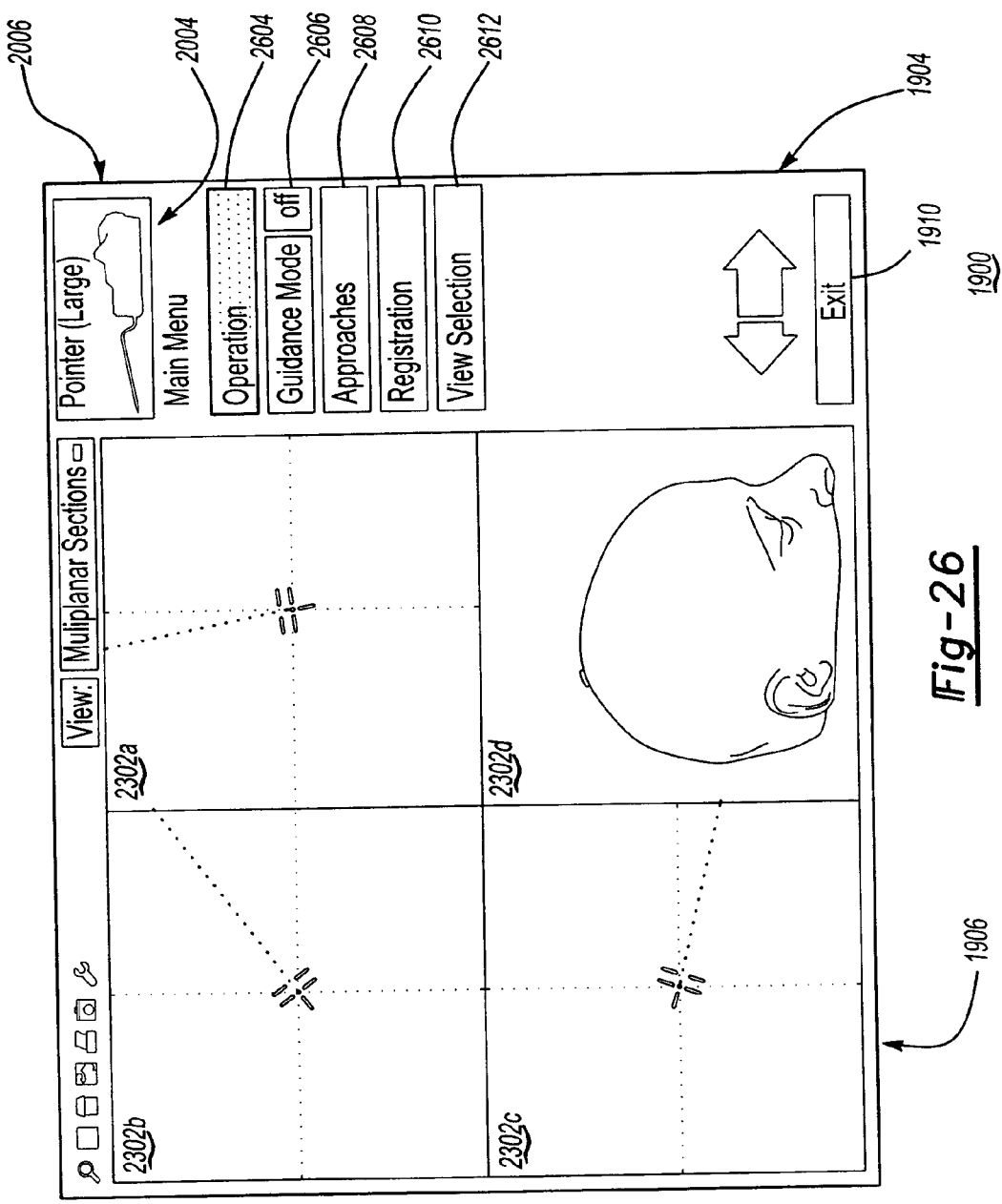
FIG. 26 is a diagrammatic illustration of the display screen of FIG. 19 with a main menu.

With reference to FIG. 26, during operation the information section 1904 includes a main menu 2602. The main menu 2602 includes an operation button 2604, a guidance mode button 2606, an approaches button 2608, a registration button 2610, and a view selection button 2612.

Figure 27:
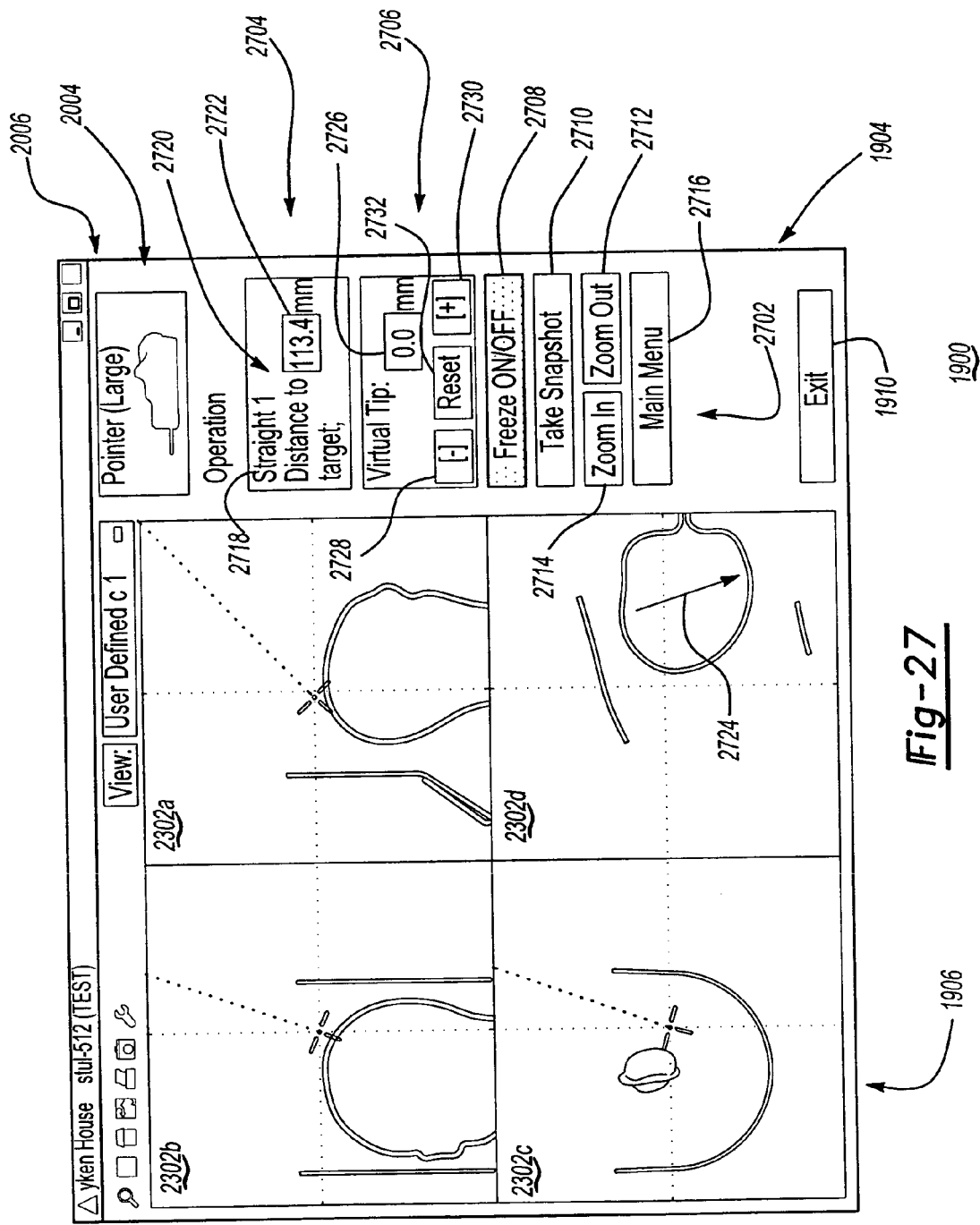
FIG. 27 is a diagrammatic illustration of the display screen of FIG. 19 during an operation mode.

With reference to FIG. 27, upon actuation of the operation button 2604 the information section 1904 includes an operation panel 2702. The operation panel 2702 includes a trajectory section 2704, a virtual tip section 2706, an image freeze toggle button 2708, a take snapshot button 2710, a zoom in button 2712, and zoom out button 2714, and a main menu button 2716.

The trajectory section 2704 includes information on the distance between the actual position of a smart instruments 102 and the desired operating point. For example, the Trajectory Section 2704 describes the type of trajectory 2720 required to reach the operating point, i.e., "Straight". A colored dot 2718 denotes the color of an image on the screen 2724 representing the trajectory. A text box 2722 contains the distance from the actual position of the smart instrument 102 and the desired operating point.

The virtual tip feature allows the operator 120 to virtually extend the tip of the smart instrument 102 on the monitor 108. This is usual for visualizing an extended instrument during operation. The virtual tip section 2706 includes a distance text box 2726, a decrementing button 2728, an incrementing button 2730 and a reset button 2732. The distance text box 2726 contains the virtual extended distance of the smart instrument 102. The decrementing button 2728, incrementing button 2730 and reset button 2732 are used to decrease, increase, and set to zero the virtual extended distance of the smart instrument and may be operated via the mouse 116 or control buttons 114.

The virtual tip feature is useful for aligning a navigated instrument along a planned trajectory. The virtual tip feature is also useful to determine the depth of a biopsy. With the tip of the smart instrument 102 placed at the entry point the distance to target is shown in the text box 2722. The virtual tip can then be extended this amount (to the target) and the alignment of the instrument along the planned trajectory is easily done.

Figure 28:
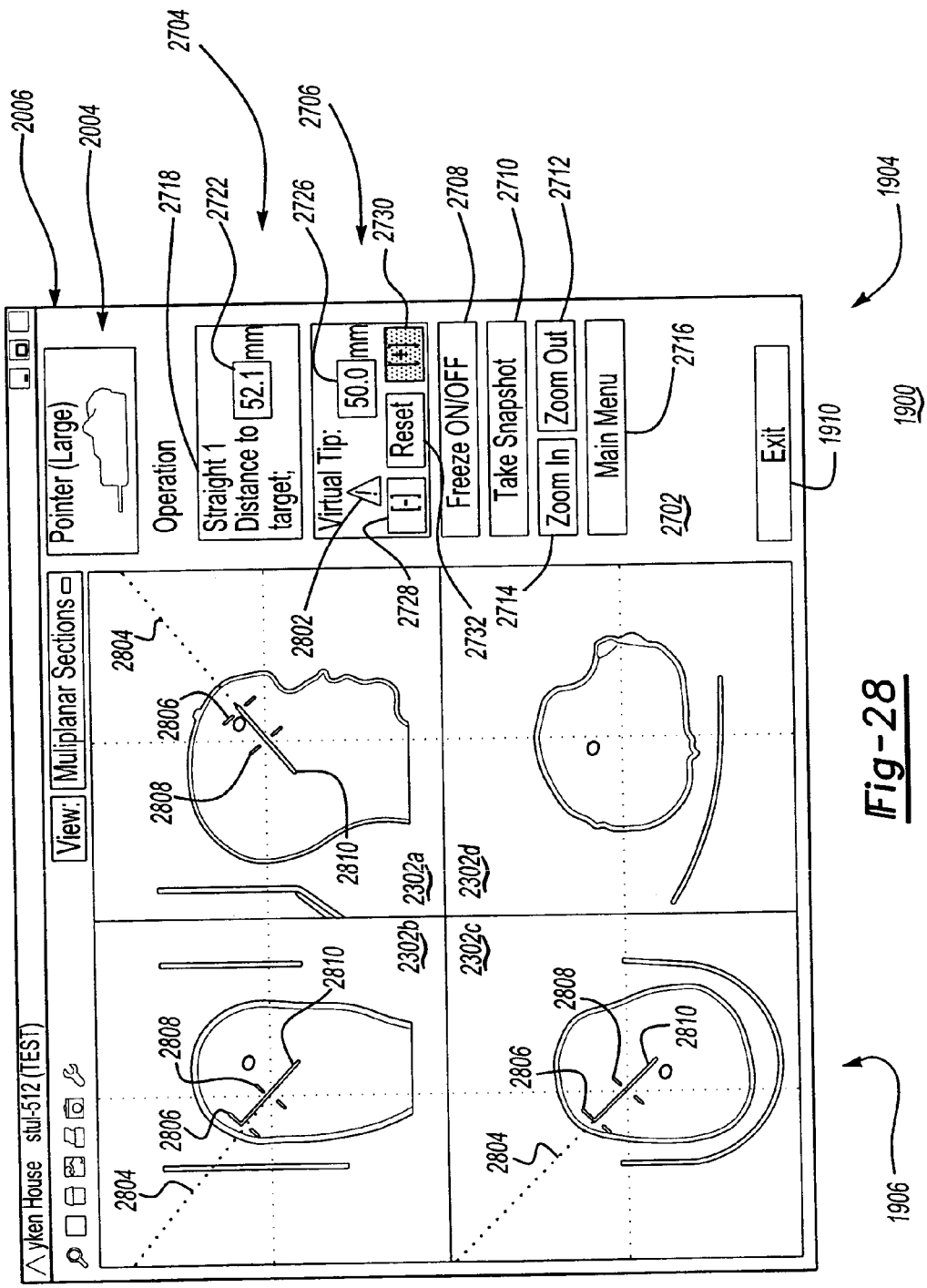
FIG. 28 is a diagrammatic illustration of the display screen of FIG. 19 during an operation mode with a virtual tip feature.

With reference to FIG. 28, a virtual tip extension of 50 mm is shown. When the tip is extended a warning signal 2802 is displayed to remind the operator 120 that a virtual probe is being displayed.

The required trajectory from the actual point of the smart instrument 102 to the desired operating point is represented by the dashed line 2804. The actual tip of the smart instrument 102 is represented by the first perpendicular line segment 2806. The second perpendicular line segment 2808 represents the virtual tip.

The freeze image toggle button 2708 is used to toggle between frozen or static onscreen images and real-time images. Real-time images are displayed during normal operation.

The take snapshot button 2710 captures the images displayed in the display section 1906 in a graphic file, preferably in a the TIFF file format, and stores the image into a patient archive.

The zoom in and zoom out buttons 2712, 2714 are used to zoom in and zoom out on the images displayed in the display section 1906.

The main menu button 2716 returns the system 100 to the main menu 2602.

Figure 29:
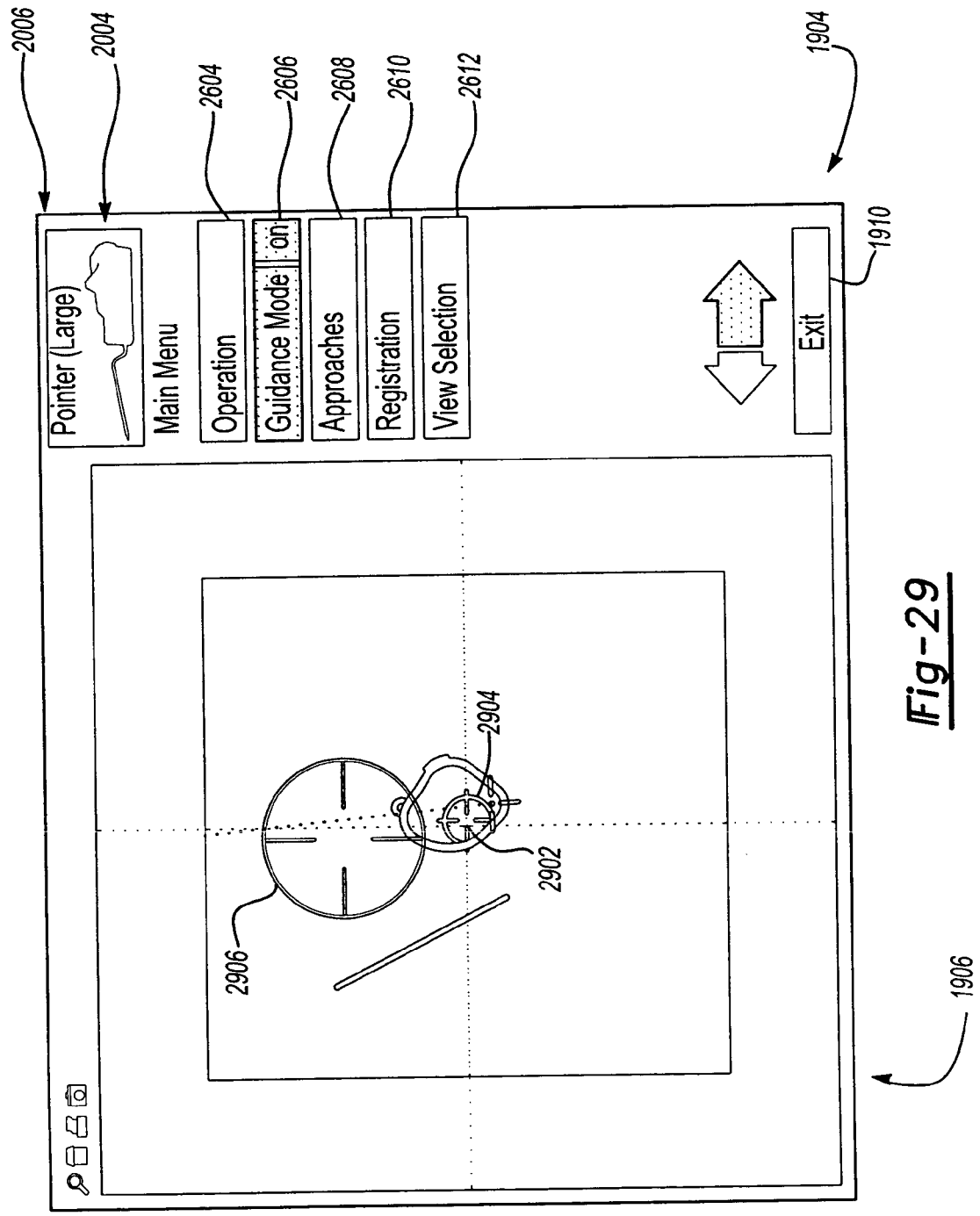
FIG. 29 is a diagrammatic illustration of the display screen of FIG. 19 during an guidance mode.
Figure 30:
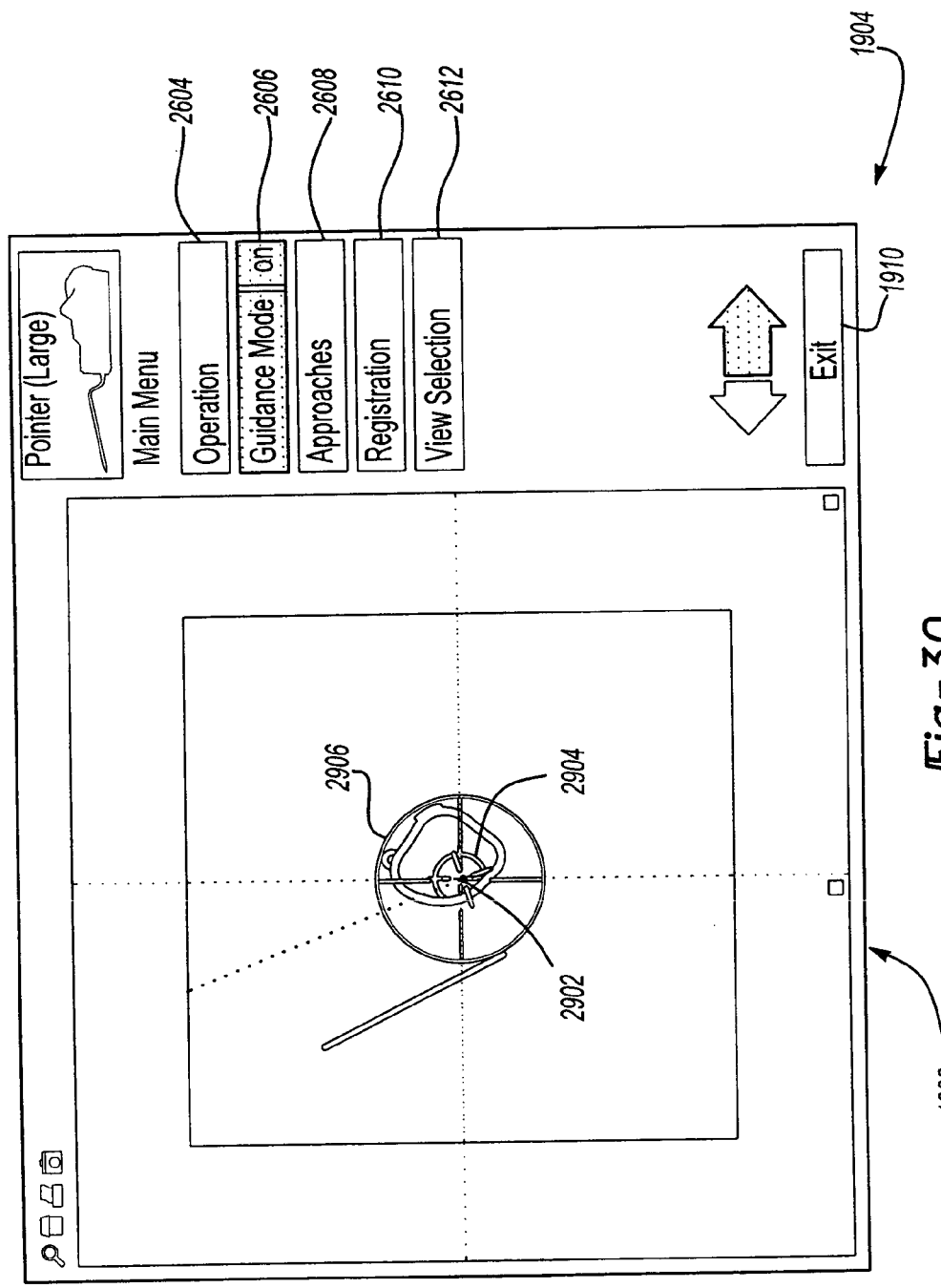
FIG. 30 is a second diagrammatic illustration of the display screen of FIG. 19 during the guidance mode.

With reference to FIGS. 29 and 30, operation of the system 100 in the guidance mode will now be explained. The guidance mode is used to guide the insertion of a smart instrument 102 into a pre-defined entry. An pre-defined entry point 2902 is displayed in the display section 1906. Preferably, the entry point 2902 remains centered in the display section 1906. A first target 2904 represents the tip of the active smart instrument 102. A second target 2906 represents the end of the smart instrument 102. The goal is to line up the first and second targets 2904, 2906 indicated that the current smart instrument 102 is at the proper orientation. The guidance mode can only be selected if there is at least one approach trajectory 2908.

Figure 31:
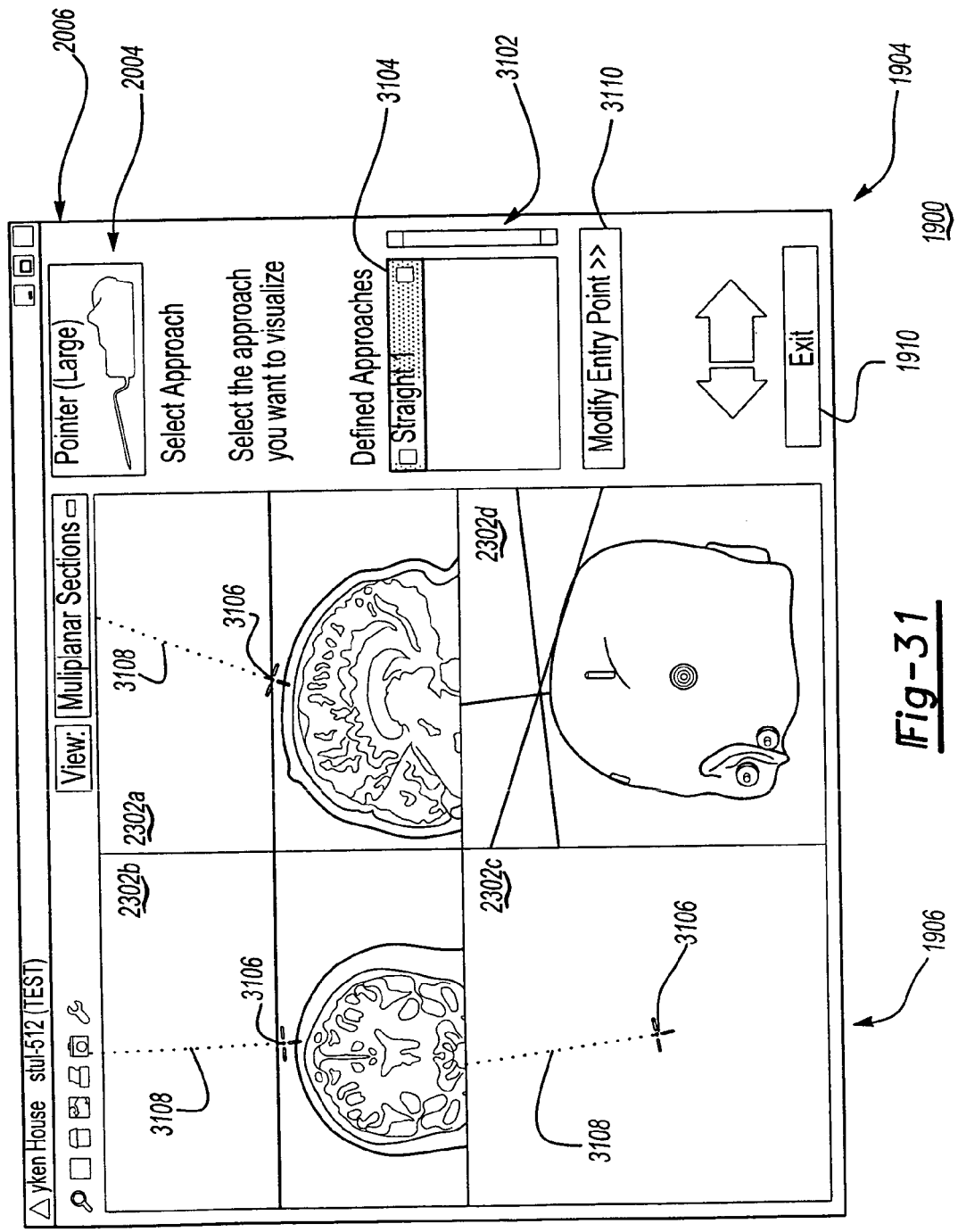
FIG. 31 is a diagrammatic illustration of the display screen of FIG. 19 during a select approach mode.
Figure 32:
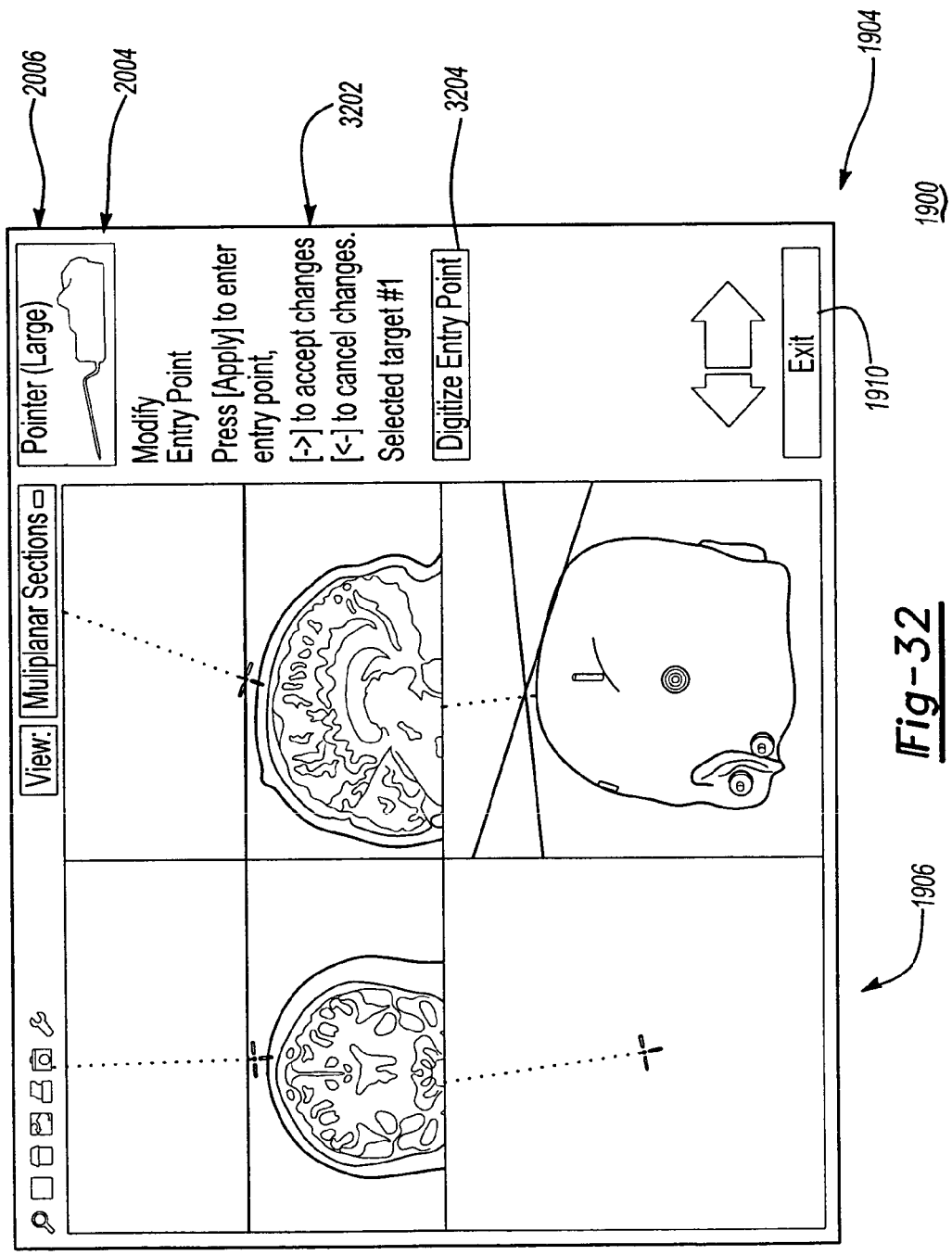
FIG. 32 is a second diagrammatic illustration of the display screen of FIG. 19 during the select approach mode.

With reference to FIGS. 31 and 32, actuation of the approaches button 2608 allows the operator 120 to view defined trajectories. With specific reference to FIG. 31, after the approaches button 2608 has been actuated, the information section 1904 includes a list 3102 of all pre-defined approaches. In this example, only one approach ("Straight 1") 3104 has been defined. One or more of the sub-sections 2302a,2302b,2302c,2302d includes an image or representation of the patient 122 illustrating the defined entry point 3106 and trajectory 3108. A modify entry point button allows the operator 120 to modify the defined entry point.

With specific reference to FIG. 32, after the modify entry point button has been actuated, the information section 1904 includes instructions 3202 on how to modify the entry point. Generally, the operator 120 places the tip of the active smart instrument 102 at a desired point and actuates the select or apply button 610 on the smart instrument 102 thereby redefining the entry point 3106. The operator 120 can then actuate either the up (forward) button 608 or the down (back) button 612 to accept or cancel the change.

With reference to FIGS. 34A and 34B, a calibration and validation tool 3400 is shown. The tool 3400 is a smart instrument having four infrared LEDs 3402a,3402b,3402c,3402d, a battery holder 3402 for a battery (not shown), a status light 3406, an infrared transceiver 3408, and a activation button 3410. When the universal tracker is mounted to a non-guided tool the calibration tool can be used calibrate the combined instruments tip position into the tracker. The calibration tool 3400 can also be used to re-calibrate another smart instrument 102 if the smart instrument 102 could not be validated (see above) or if it is suspected that the smart took 102 has been compromised. Additionally, the calibration tool 3400 can be used to validate another smart instrument 102 if, for example, a patient tracker system 502 with a universal tracker device 200 is not being used.

Like all smart instruments 102, the calibration tool 3400 must be initialized. The calibration tool 3400 must be placed on a solid surface within the working volume of the system 100 with the LEDs 3402a,3402b,3402c,3402d in view of the sensor system 104. Then it is initialized through actuation of the activation button 3410 (see above).

The calibration tool 3400 includes at least one validation point 3412. In the preferred embodiment, the tool 3400 includes four validation points 3412a,3412b,3412c,3412d adapted to various types of tool tips. The four validation points 3412a,3412b,3412c,3412d are mounted at the top of four columns 3414a,3414b,3414c,3414d. The four columns 3414a,3414b,3414c,3414d are coupled to a base 3416. An, upper and lower plate 3418,3420 are slidably coupled to the four columns 3414a,3414b,3414c,3414d. First and second upper platform screws 3418a,3418b and first and second lower platform screws 3420a,3420b lock the upper and lower plates 3418,3420 to the four columns 3414a,3414b,3414c,3414d, respectively.

The upper plate 3418 includes a first aperture 3422. A first lever 3424 is coupled to a first plurality of flanges 3426. The first lever 3424 operates the first plurality of flanges to variably close and/or change the size of the first aperture 3422.

The lower plate 3420 includes a second aperture 3428. A second lever 3430 is coupled to a second plurality of flanges 3432. The second lever 3430 operates the second plurality of flanges 3432 to variably close and/or change the size of the second aperture 3428.

Figure 35:
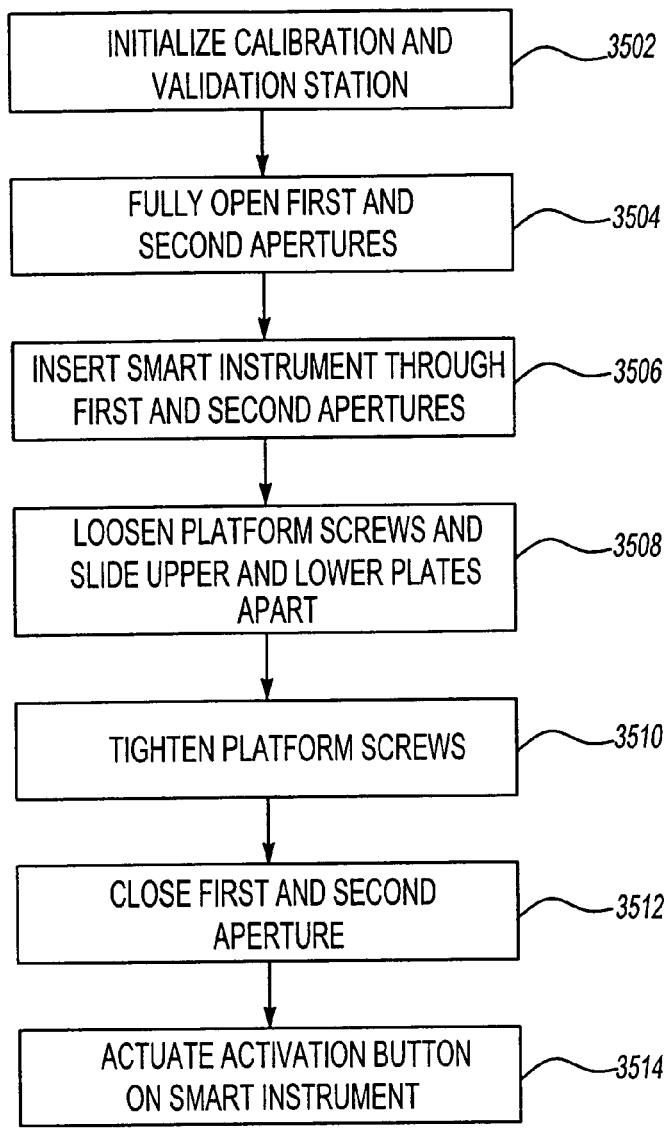
FIG. 35 is a flow diagram of a calibration process for a smart instrument using the calibration and validation tool of FIGS. 34A and 34B, according to an embodiment of the present invention; and, FIG. 36 is a perspective view of a remote control device, according to an embodiment of the present invention.

With reference to FIG. 35, the process to calibrate a smart instrument 102 will now be explained. In a thirteenth process block 3502, the station 3400 is initialized (see above). In a fourteenth process block 3504, the first and second apertures 3422, 3428 are fully opened via the first and second levers 3424,3430, respectively.

In a fifteenth process block 3506, the smart instrument 102 to be calibrated is then inserted through the first and second apertures 3422, 3428 until the tip of the smart instrument 102 is against the base 3416.

In a sixteenth process block 3508, the platform screws 3418a,3418b,3418c,3418d are loosened and the upper and lower plates 3418, 3420 are slid apart as far as the shape of the smart instrument 102 allows.

In a seventeenth process block 3410, the platform screws 3418a,3418b,3420a,3420b are then tightened.

In an eighteenth process block 3412, the first and second levers 3424,3430 are used to close the first and second apertures 3422,3428 around the smart instrument 102.

In a nineteenth process block 3414, the operator 120 then presses the activation button 214 or select button 610 on the smart instrument 102. The LEDs 202, 604 on the smart instrument 102 are then read by the localizer system. Position information is relayed to the computer system 106 which calculates new calibration information for the smart instrument 102. In the preferred embodiment, the new calibration information is then sent back to the smart instrument 102 and stored thereon. Whenever this smart instrument is thereafter activated, the new calibration is then sent to the computer system 106 for use.

It is recommended that after a smart instrument has been calibrated, that it be validated. The calibration and validation tool 3400 can also be used to perform the validation. The operation of the calibration and validation tool 3400 to validate a smart instrument 102 is similar to the use of the universal tracker device 200.

Figure 36:
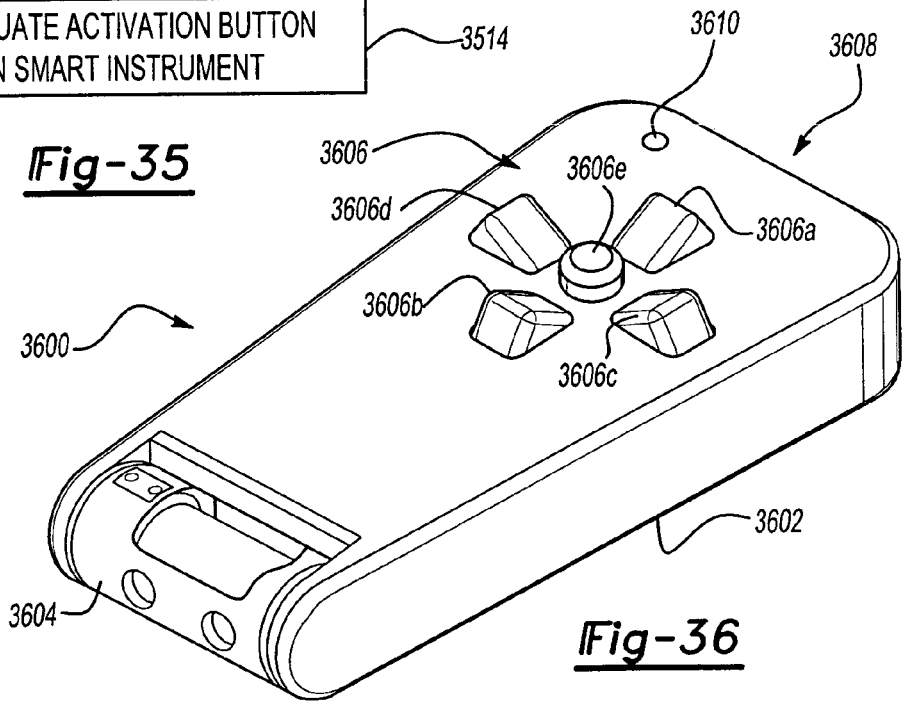

With reference to FIG. 36, the system 100 includes a remote control device 3600 which allows the operator 120 to move through and make selections from the display screen 1900 on the monitor 108. Preferably, the remote control device 3600 can be sterilized and placed with the work volume of the system.

The remote control device 3600 includes a housing 3602 with a battery holder 3604. A plurality of control buttons 3606 allow the operator 120 to control the system 100, an infrared transceiver 3608 and a status light 3610. In the preferred embodiment, the remote control device 3600 includes an upward button 3606a, a downward button 3606b, a next button 3606c, a back button 3606D, and a select or apply button 3606E.

As discussed above, the system 100 operates on a scanning cycle which has a length based on the number of smart instruments 102 active. At the beginning of each cycle, the system 100 sends out a new tool inquiry package system which requests that any new smart instruments 102 identify themselves (see above). If there are no new tools, then the system 100 cycles through the active smart instruments 102 to determine their position.

In order to determine a smart instrument's 102 position, the system 100 has stored the number of LEDs in each smart instrument 102 that has been activated. Only one LED 202, 604 can be read at a time.

In the preferred embodiment, the system 100 first sends out a initial signal identifying a smart instrument 102 by serial number that it should prepare for firing its LEDs 202, 604. The initial signal also request status information from the targeted smart instrument 102. This status information may include battery life, any faults, activated control buttons, etc. . . . The target smart instrument 102 delivers the requested status information to the system 100.

The initial signal may also include commands for the smart instrument 102. For example, for a smart instrument 102 adapted as an irrigator may respond to on and off commands.

The system 100 then requests that the smart instrument 102 fires off each LED one at a time in order to be recognized by the system 100.

In one embodiment, the system 100 cycles through all active smart instruments and attempts to determine their position.

In another embodiment, the system 100 only determines the position of any universal tracker device 200 coupled to a patient tracked system 502 and a smart tool 102 currently being used by the operator 120. In this embodiment, when the operator 120 picks up (an already activated) smart instrument 102, the operator 120 must actuate the activation button 214 or the select button 610. This signals to the system 100 that the smart instrument 102 is currently being used. In the preferred embodiment, the system 100 cycles through all active instruments 102 but temporarily sets the number of LEDs on the instruments 102 not being used to zero (0).

As discussed above, the control buttons 114 are programmable and are adapted to operate, i.e., navigate through, the software running on the computer system 106. The control buttons 114 are also used in the validation and calibration operations, as discussed above. For example, on the smart instrument 600 shown in FIG. 6, the select button 610 is used to validate the smart instrument 600, calibrate the instrument 600 and activate the instrument 600. The system 600, based on the position of the smart instrument 600 performs the correct operation. For example, if the smart instrument 600 position indicates that the pointer 614 is located at the validation point 216 of the universal tracker device 200 (or the validation tool 3400), then the system 100 performs a validation operation upon activation of the select button 610. If the smart instrument 600 is in the calibration tool 3400, then a calibration operation is performed when the select button 610 is activated. This feature can also be used with other input devices to the system 100. For example, if the operator 120 needs to push a button on the keyboard 116, the operator 120 can simply point at the desired key and activate the select button 610.

Other aspects, objects, and features of the present invention can be obtained from a study of the drawings, the disclosure, and the appended claims.

The invention claimed is:

1. A surgery system, comprising:
   at least two smart instruments, wherein each smart instrument comprises a housing, a plurality of LEDs coupled with the housing and adapted to fire independently, and a first transceiver;
   a computer system having a scanning cycle the length of which is dependant on the number of smart instruments to be tracked; and
   a sensor system adapted to wirelessly sense the position of the at least two smart instruments and to transmit position information to the computer system, wherein the sensor system includes a sensor array comprising a plurality of position sensors and at least a second transceiver; and
   wherein the surgery system temporarily sets the number of LEDs to be activated on an unused active smart instrument to zero, and wherein during each scanning cycle the surgery system cycles successively through all of the smart instruments and the second transceiver wirelessly transmits an instruction to the first transceiver of each of the smart instruments in consecutive order that have a number of LEDs that have not been set to zero, that causes the LEDs thereof to fire independently one at a time in order to be recognized by the surgery system.

2. A surgery system, as set forth in claim 1, wherein the computer system includes a monitor and wherein the computer system is adapted to display a diagram of a patient on the monitor.

3. A surgery system, as set forth in claim 2, wherein the computer system is adapted to display a representation of one of the at least two smart instruments on the diagram.

4. A surgery system, as set forth in claim 3, wherein the one of the at least two smart instruments is in use.

5. A surgery system, as set forth in claim 4, wherein the computer system is adapted to alternatively determine the position of the at least two smart instruments.

* * * * *